US005721128A

United States Patent [19]

Deweer et al.

[11] Patent Number: 5,721,128
[45] Date of Patent: Feb. 24, 1998

[54] PROCESS FOR THE PRODUCTION OF NOVEL PULLULANASE

[75] Inventors: Philippe Deweer, Aalst; Antoine Amory, Rixensart, both of Belgium

[73] Assignee: Genencor International, Inc., Rochester, N.Y.

[21] Appl. No.: 477,630

[22] Filed: Jun. 7, 1995

Related U.S. Application Data

[62] Division of Ser. No. 174,893, Dec. 28, 1993, abandoned.

[30] Foreign Application Priority Data

Dec. 28, 1992 [BE] Belgium ............................. 09201156
Jul. 15, 1993 [BE] Belgium ............................. 09300744
Nov. 19, 1993 [BE] Belgium ............................. 09301278

[51] Int. Cl.$^6$ ........................................................ C12N 9/44
[52] U.S. Cl. ................................................................ 435/210
[58] Field of Search ................................................. 435/210

[56] References Cited

U.S. PATENT DOCUMENTS

| | | | |
|---|---|---|---|
| 4,560,651 | 12/1985 | Nielsen et al. | 435/95 |
| 4,612,287 | 9/1986 | Coleman et al. | 435/172.3 |
| 4,628,028 | 12/1986 | Katkocin et al. | 435/95 |
| 4,628,031 | 12/1986 | Zeikus | 435/205 |
| 4,902,622 | 2/1990 | Nakai et al. | 435/210 |
| 5,055,403 | 10/1991 | Tomimura | 435/210 |
| 5,281,527 | 1/1994 | Tachibana et al. | 435/210 |
| 5,316,924 | 5/1994 | Takasaki | 435/71.2 |
| 5,387,516 | 2/1995 | Kawai et al. | 435/210 |

FOREIGN PATENT DOCUMENTS

| | | |
|---|---|---|
| 0 063 909A1 | 11/1982 | European Pat. Off. . |
| 0 063 909B2 | 9/1990 | European Pat. Off. . |
| 0 405 283A2 | 1/1991 | European Pat. Off. . |

OTHER PUBLICATIONS

Norman, "A Novel Bacillus Pullulanase—Its Properties and Application in the Glucose Syrups Industry," J. Jpn. Soc. Starch Sci., vol. 30, No. 2 (1983), pp. 200–211.

Harwood et al., "Molecular Biological Methods for Bacillus," John Wiley and Sons (1990), pp. 150–151.

Manners, "Structural Analysis of Starch Components by Debranching Enzymes, New Approaches to Research on Cereal Carbohydrates", Edited by R.D. Hill and L. Munck, Elsevier Science Publishers B.V., Amsterdam, (1985), pp. 45–54.

Enevoldsen, "Aspects of the Fine Structure of Starch," New Approaches to Research on Cereal Carbohydrates, Edited by R.D. Hill and L. Munck, Elsevier Science Publishers B.V., Amsterdam, (1985), pp. 55–60.

Maniatis et al., "Molecular Cloning," A Laboratory Manual, Cold Spring Harbor Laboratory (1982), pp. 150–152 and 374–379.

Freudl, "Protein Secretion in Gram–Positive Bacteria," Journal of Biotechnology, vol. 23 (1992), pp. 231–240.

Sullivan et al., "New Shuttle Vectors for *Bacillus subtilis* and *Escherichia coli* Which Allows Rapid Detection of Inserted Fragments," Gene, vol. 29 (1984), pp. 21–26.

Sanger et al., "DNA Sequencing with Chain–Terminating Inhibitors," Proc. Natl. Acad. Sci. USA, vol. 74, No. 12 (Dec. 1977), pp. 5463–5467.

Beaucage et al., "Deoxynucleoside Phosphoramidites—A New Class of Key Intermediates for Deoxypolynucleotide Synthesis," Tetrahedron Letters, vol. 22, No. 20 (1981), pp. 1859–1862.

Molecular Cloning—A Laboratory Manual—Sambrook, Fritsch, Maniatis—Second Edition (1989).

Norton Nelson, "A Photometric Adaptation of the Somogyi Method for the Determination of Glucose," J. Biol. Chem., vol. 153 (1944), pp. 375–380.

Michael Somogyi, "A New Reagent for the Determination of Sugars," J. Biol. Chem., vol. 160 (1945), pp. 61–68.

Bauw et al., "Alterations in the Phenotype of Plant Cells Studied $NH_2$–Terminal Amino Acid–Sequence Analysis of Proteins Electroblotted from Two–Dimensional Gel–Separated Total Extracts," Proc. Natl. Acad. Sci. USA, vol. 84 (1987), pp. 4806–4810.

Takashi Kuriki et al., "New Type of Pullulanase from *Bacillus stearothermophilus* and Molecular Cloning and Expression of the Gene in *Bacillus subtilis*," Journal of Bacteriology, vol. 170, No. 4, pp. 1554–1559 (Apr., 1988).

European Search Report dated Mar. 10, 1994, in Corresponding European Patent Publication No. 93 20 3593.

Jensen, et al., "*Bacillus acidopullulyticus* Pullulanase: Application and Regulatory Aspects for Use in the Food Industry", Process Biochemistry, pp. 129–134 (Aug. 1984).

Primary Examiner—Robert A. Wax
Assistant Examiner—Lisa J. Hobbs
Attorney, Agent, or Firm—Cooley Godward LLP

[57] ABSTRACT

The invention relates to a heat-stable pullulanase having the property of hydrolysing glucosidic bonds of the $\alpha$-1,6 type in amylopectin and having an enzymatic activity in an acid medium and at a temperature of about 60° C.

The invention also relates to strains of micro-organisms which produce this pullulanase and processes for the preparation of this pullulanase.

The invention also relates to the uses thereof and compositions comprising the product.

The invention also relates to a DNA molecule. The invention relates to an expression vector containing this DNA molecule and to a chromosomal integration vector containing this DNA molecule.

1 Claim, 14 Drawing Sheets

|                                                                                                                                  |     |
| -------------------------------------------------------------------------------------------------------------------------------- | --- |
| GAT GGG AAC ACG ACA ACG<br>Asp Gly Asn Thr Thr Thr<br>+1           5                                                             | 18  |
| ATC ATT GTC CAC TAT TTT TGC CCT GCT GGT GAT TAT CAA<br>Ile Ile Val His Tyr Phe Cys Pro Ala Gly Asp Tyr Gln<br>        10              15 | 57  |
| CCT TGG AGT CTA TGG ATG TGG CCA AAA GAC GGA GGT GGG<br>Pro Trp Ser Leu Trp Met Trp Pro Lys Asp Gly Gly Gly<br>20              25              30 | 96  |
| GCT GAA TAC GAT TTC AAT CAA CCG GCT GAC TCT TTT GGA<br>Ala Glu Tyr Asp Phe Asn Gln Pro Ala Asp Ser Phe Gly<br>        35              40              45 | 135 |
| GCT GTT GCA AGT GCT GAT ATT CCA GGA AAC CCA AGT CAG<br>Ala Val Ala Ser Ala Asp Ile Pro Gly Asn Pro Ser Gln<br>            50              55     | 174 |
| GTA GGA ATT ATC GTT CGC ACT CAA GAT TGG ACC AAA GAT<br>Val Gly Ile Ile Val Arg Thr Gln Asp Trp Thr Lys Asp<br>60              65              70 | 213 |
| GTG AGC GCT GAC CGC TAC ATA GAT TTA AGC AAA GGA AAT<br>Val Ser Ala Asp Arg Tyr Ile Asp Leu Ser Lys Gly Asn<br>        75              80          | 252 |
| GAG GTG TGG CTT GTA GAA GGA AAC AGC CAA ATT TTT TAT<br>Glu Val Trp Leu Val Glu Gly Asn Ser Gln Ile Phe Tyr<br>85              90              95 | 291 |
| AAT GAA AAA GAT GCT GAG GAT GCA GCT AAA CCC GCT GTA<br>Asn Glu Lys Asp Ala Glu Asp Ala Ala Lys Pro Ala Val<br>        100             105             110 | 330 |
| AGC AAC GCT TAT TTA GAT GCT TCA AAC CAG GTG CTG GTT<br>Ser Asn Ala Tyr Leu Asp Ala Ser Asn Gln Val Leu Val<br>            115             120    | 369 |
| AAA CTT AGC CAG CCG TTA ACT CTT GGG GAA GGN NNA AGC<br>Lys Leu Ser Gln Pro Leu Thr Leu Gly Glu Gly Xaa Ser<br>125             130             135 | 408 |
| GGC TTT ACG GTT CAT GAC GAC ACA GCA AAT AAG GAT ATT<br>Gly Phe Thr Val His Asp Asp Thr Ala Asn Lys Asp Ile<br>        140             145        | 447 |

*FIG. 4A*

| | | |
|---|---|---|
| CCA GTG ACA TCT GTG AAG GAT GCA AGT CTT GGT CAA GAT<br>Pro Val Thr Ser Val Lys Asp Ala Ser Leu Gly Gln Asp<br>150                   155                        160 | | 486 |
| GTA ACC GCT GTT TTG GCA GGT ACC TTC CAA CAT ATT TTT<br>Val Thr Ala Val Leu Ala Gly Thr Phe Gln His Ile Phe<br>            165                     170                 175 | | 525 |
| GGA GGT TCC GAT TGG GCA CCT GAT AAT CAC AGT ACT TTA<br>Gly Gly Ser Asp Trp Ala Pro Asp Asn His Ser Thr Leu<br>               180                   185 | | 564 |
| TTA AAA AAG GTG ACT AAC AAT CTC TAT CAA TTC TCA GGA<br>Leu Lys Lys Val Thr Asn Asn Leu Tyr Gln Phe Ser Gly<br>    190                      195                 200 | | 603 |
| GAT CTT CCT GAA GGA AAC TAC CAA TAT AAA GTG GCT TTA<br>Asp Leu Pro Glu Gly Asn Tyr Gln Tyr Lys Val Ala Leu<br>            205                         210 | | 642 |
| AAT GAT AGC TGG AAT AAT CCG AGT TAC CCA TCT GAC AAC<br>Asn Asp Ser Trp Asn Asn Pro Ser Tyr Pro Ser Asp Asn<br>215                   220                       225 | | 681 |
| ATT AAT TTA ACA GTC CCT GCC GGC GGT GCA CAC GTC ACT<br>Ile Asn Leu Thr Val Pro Ala Gly Gly Ala His Val Thr<br>    230                           235               240 | | 720 |
| TTT TCG TAT ATT CCG TCC ACT CAT GCA GTC TAT GAC ACA<br>Phe Ser Tyr Ile Pro Ser Thr His Ala Val Tyr Asp Thr<br>                   245                        250 | | 759 |
| ATT AAT AAT CCT AAT GCG GAT TTA CAA GTA GAA AGC GGG<br>Ile Asn Asn Pro Asn Ala Asp Leu Gln Val Glu Ser Gly<br>255                   260                       265 | | 798 |
| GTT AAA ACG GAT CTC GTG ACG GTT ACT CTA GGG GAA GAT<br>Val Lys Thr Asp Leu Val Thr Val Thr Leu Gly Glu Asp<br>            270                        275 | | 837 |
| CCA GAT GTG AGC CAT ACT CTG TCC ATT CAA ACA GAT GGC<br>Pro Asp Val Ser His Thr Leu Ser Ile Gln Thr Asp Gly<br>280                   285                       290 | | 876 |
| TAT CAG GCA AAG CAG GTG ATA CCT CGT AAT GTG CTT AAT<br>Tyr Gln Ala Lys Gln Val Ile Pro Arg Asn Val Leu Asn<br>            295                      300              305 | | 915 |
| TCA TCA CAG TAC TAC TAT TCA GGA GAT GAT CTT GGG AAT<br>Ser Ser Gln Tyr Tyr Tyr Ser Gly Asp Asp Leu Gly Asn<br>                   310                        315 | | 954 |

FIG. 4B

| | | | | | | | | | | | |
|---|---|---|---|---|---|---|---|---|---|---|---|
| ACC | TAT | ACA | CAG | AAA | GCA | ACA | ACC | TTT | AAA | GTC | TGG GCA | 993 |
| Thr | Tyr | Thr | Gln | Lys | Ala | Thr | Thr | Phe | Lys | Val | Trp Ala |
| | 320 | | | | | 325 | | | | | 330 |

```
ACC TAT ACA CAG AAA GCA ACA ACC TTT AAA GTC TGG GCA        993
Thr Tyr Thr Gln Lys Ala Thr Thr Phe Lys Val Trp Ala
    320             325                     330

CCA ACT TCT ACT CAA GTA AAT GTT CTT CTT TAT GAC AGT       1032
Pro Thr Ser Thr Gln Val Asn Val Leu Leu Tyr Asp Ser
        335             340

GCA ACG GGT TCT GTA ACA AAA ATC GTA CCT ATG ACG GCA       1071
Ala Thr Gly Ser Val Thr Lys Ile Val Pro Met Thr Ala
345             350              355

TCG GGC CAT GGT GTG TGG GAA GCA ACG GTT AAT CAA AAC       1110
Ser Gly His Gly Val Trp Glu Ala Thr Val Asn Gln Asn
        360              365                 370

CTT GAA AAT TGG TAT TAC ATG TAT GAG GTA ACA GGC CAA       1149
Leu Glu Asn Trp Tyr Tyr Met Tyr Glu Val Thr Gly Gln
            375              380

GGC TCT ACC CGA ACG GCT GTT GAT CCT TAT GCA ACT GCG       1188
Gly Ser Thr Arg Thr Ala Val Asp Pro Tyr Ala Thr Ala
    385              390              395

ATT GCA CCA AAT GGA ACG AGA GGC ATG ATT GTG GAC CTG       1227
Ile Ala Pro Asn Gly Thr Arg Gly Met Ile Val Asp Leu
            400              405

GCT AAA ACA GAT CCT GCT GGC TGG AAC AGT GAT AAA CAT       1266
Ala Lys Thr Asp Pro Ala Gly Trp Asn Ser Asp Lys His
410             415                  420

ATT ACG CCA AAG AAT ATA GAA GAT GAG GTC ATC TAT GAA       1305
Ile Thr Pro Lys Asn Ile Glu Asp Glu Val Ile Tyr Glu
        425              430                  435

ATG GAT GTC CGT GAC TTT TCC ATT GAC CCT AAT TCG GGT       1344
Met Asp Val Arg Asp Phe Ser Ile Asp Pro Asn Ser Gly
            440              445

ATG AAA AAT AAA GGG AAG TAT TTG GCT CTT ACA GAA AAA       1383
Met Lys Asn Lys Gly Lys Tyr Leu Ala Leu Thr Glu Lys
    450             455                  460

GGA ACA AAG GGC CCT GAC AAC GTA AAG ACG GGG ATA GAT       1422
Gly Thr Lys Gly Pro Asp Asn Val Lys Thr Gly Ile Asp
            465              470

TCC TTA AAA CAA CTT GGG ATT ACT CAT GTT CAG CTT ATG       1461
Ser Leu Lys Gln Leu Gly Ile Thr His Val Gln Leu Met
475             480                  485
```

FIG. 4C

```
CCT GTT TTC GCA TCT AAC AGT GTC GAT GAA ACT GAT CCA        1500
Pro Val Phe Ala Ser Asn Ser Val Asp Glu Thr Asp Pro
        490                 495                 500

ACC CAA GAT AAT TGG GGT TAT GAC CCT CGC AAC TAT GAT        1539
Thr Gln Asp Asn Trp Gly Tyr Asp Pro Arg Asn Tyr Asp
                505                 510

GTT CCT GAA GGG CAG TAT GCT ACA AAT GCG AAT GGT AAT        1578
Val Pro Glu Gly Gln Tyr Ala Thr Asn Ala Asn Gly Asn
        515                 520                 525

GCT CGT ATA AAA GAG TTT AAG GAA ATG GTT CTT TCA CTC        1617
Ala Arg Ile Lys Glu Phe Lys Glu Met Val Leu Ser Leu
                530                 535

CAT CGT GAA CAC ATT GGG GTT AAC ATG GAT GTT GTC TAT        1656
His Arg Glu His Ile Gly Val Asn Met Asp Val Val Tyr
540                 545                 550

AAT CAT ACC TTT GCC ACG CAA ATC TCT GAC TTC GAT AAA        1695
Asn His Thr Phe Ala Thr Gln Ile Ser Asp Phe Asp Lys
        555                 560                 565

ATT GTA CCA GAA TAT TAT TAC CGT ACG ATG ATG CAG GTA        1734
Ile Val Pro Glu Tyr Tyr Tyr Arg Thr Met Met Gln Val
                570                 575

ATT ATA CCA ACG GAT CAG GTA CTG GAA ATG AAA TTG CAN        1773
Ile Ile Pro Thr Asp Gln Val Leu Glu Met Lys Leu Xaa
        580                 585                 590

GCN GAA AGG CCA ATG GTT CAA AAA TTT ATT ATT GAT TCC        1812
Ala Glu Arg Pro Met Val Gln Lys Phe Ile Ile Asp Ser
                595                 600

CTT AAG TAT TGG GTC AAT GAG TAT CAT ATT GAC GGC TTC        1851
Leu Lys Tyr Trp Val Asn Glu Tyr His Ile Asp Gly Phe
605                 610                 615

CGT TTT GAC TTA ATG GCG CTG CTT GGA AAA GAC ACG ATG        1890
Arg Phe Asp Leu Met Ala Leu Leu Gly Lys Asp Thr Met
        620                 625                 630

TCC AAA GCT GCC TCG GAG CTT CAT GCT ATT AAT CCA GGA        1929
Ser Lys Ala Ala Ser Glu Leu His Ala Ile Asn Pro Gly
                635                 640

ATT GCA CTT TAC GGT GAG CCA TGG ACG GGT GGA ACC TCT        1968
Ile Ala Leu Tyr Gly Glu Pro Trp Thr Gly Gly Thr Ser
645                 650                 655
```

*FIG. 4D*

```
GCA CTG CCA GAT GAT CAG CTT CTG ACA AAA GGA GCT CAA                    2007
Ala Leu Pro Asp Asp Gln Leu Leu Thr Lys Gly Ala Gln
            660             665

AAA GGC ATG GGA GTA GCG GTG TTT AAT GAC AAT TTA CGA                    2046
Lys Gly Met Gly Val Ala Val Phe Asn Asp Asn Leu Arg
670             675             680

AAC GCG TTG GAC GGC AAT GTC TTT GAT TCT TCC GCT CAA                    2085
Asn Ala Leu Asp Gly Asn Val Phe Asp Ser Ser Ala Gln
        685             690             695

GGT TTT GCG ACA GGT GCA ACA GGC TTA ACT GAT GCA ATT                    2124
Gly Phe Ala Thr Gly Ala Thr Gly Leu Thr Asp Ala Ile
                700             705

AAG AAT GGC GTT GAG GGG AGT ATT AAT GAC TTT ACC TCT                    2163
Lys Asn Gly Val Glu Gly Ser Ile Asn Asp Phe Thr Ser
    710             715             720

TCA CCA GGT GAG ACA ATT AAC TAT GTC ACA AGT CAT GAT                    2202
Ser Pro Gly Glu Thr Ile Asn Tyr Val Thr Ser His Asp
            725             730

AAC TAC ACC CTT TGG GAC AAA ATA GCC CTA AGC AAT CCT                    2241
Asn Tyr Thr Leu Trp Asp Lys Ile Ala Leu Ser Asn Pro
735             740             745

AAT GAT TCC GAA GCG GAT CGG ATT AAA ATG GAT GAA CTC                    2280
Asn Asp Ser Glu Ala Asp Arg Ile Lys Met Asp Glu Leu
        750             755             760

GCA CAA GCA GTT GTT ATG ACC TCA CAA GGC GTT CCA TTC                    2319
Ala Gln Ala Val Val Met Thr Ser Gln Gly Val Pro Phe
                765             770

ATG CAA GGC GGG GAA GAA ATG CTT CGT ANA AAA GGC GGC                    2358
Met Gln Gly Gly Glu Glu Met Leu Arg Xaa Lys Gly Gly
    775             780             785

AAC GAC AAT AGT TAT AAT GCA GGC GAT GCG GTC AAT GAG                    2397
Asn Asp Asn Ser Tyr Asn Ala Gly Asp Ala Val Asn Glu
            790             795

TTT GAT TGG AGC AGG AAA GCT CAA TAT CCA GAT GTT TTC                    2436
Phe Asp Trp Ser Arg Lys Ala Gln Tyr Pro Asp Val Phe
800             805             810

AAC TAT TAT AGC GGG CTA ATC CAC CTT CGT CTT GAT CAC                    2475
Asn Tyr Tyr Ser Gly Leu Ile His Leu Arg Leu Asp His
        815             820             825
```

FIG. 4E

```
CCA GCC TTC CGC ATG ACG ACA GCT AAT GAA ATC AAT AGC                      2514
Pro Ala Phe Arg Met Thr Thr Ala Asn Glu Ile Asn Ser
            830                 835

CAC CTC CAA TTC CTA AAT AGT CCA GAG AAC ACA GTG GCC                      2553
His Leu Gln Phe Leu Asn Ser Pro Glu Asn Thr Val Ala
    840                 845                 850

TAT GAA TTA ACT GAT CAT GTT AAT AAA GAC AAA TGG GGA                      2592
Tyr Glu Leu Thr Asp His Val Asn Lys Asp Lys Trp Gly
            855                 860

AAT ATC ATT GTT GTT TAT AAC CCA AAT AAA ACT GTA GCA                      2631
Asn Ile Ile Val Val Tyr Asn Pro Asn Lys Thr Val Ala
865                 870                 875

ACC ATC AAT TTG CCG AGC GGG AAA TGG GCA ATC AAT GCT                      2670
Thr Ile Asn Leu Pro Ser Gly Lys Trp Ala Ile Asn Ala
            880                 885                 890

ACG AGC GGT AAG GTA GGA GAA TCC ACC CTT GGT CAA GCA                      2709
Thr Ser Gly Lys Val Gly Glu Ser Thr Leu Gly Gln Ala
                895                 900

GAG GGA AGT GTC CAA GTA CCA GGT ATA TCT ATG ATG ATC                      2748
Glu Gly Ser Val Gln Val Pro Gly Ile Ser Met Met Ile
905                 910                 915

CTT CAT CAA GAG GTA AGC CCA GAC CAC GGT AAA AAG                          2784
Leu His Gln Glu Val Ser Pro Asp His Gly Lys Lys
            920                 925
```

*FIG. 4F*

| | |
|---|---:|
| GGATCCTGTT AGACTATTTG AGGAGTTTGC AACACTTGAT GTTTTATCCA | 50 |
| AAGGAAGGGC CGGAGATCAT CGCTGGTCGA GGTGCTTTCG GTGAAGCATT | 100 |
| TTCGCTATTT TGGGTATAAC CGGGCGCATT ACGATCAATT GTTTGAAGAG | 150 |
| CATCTTGATT TACTTCAAAA GCTGAATGCT TCGAAAAGAA TAACATGGAG | 200 |
| CGGGCTTTAT CGAACACCTA TACATGATGC AGATATCGCA CCCCGCCCTG | 250 |
| TTCAGAAAAA CATTCCTTTG TGGGTTGGGG TGGGTGGGAC NMNTGAAASC | 300 |
| NSYKCKYYGT GCRNVSNNNT ATGGTGCCGG CTTAGCATGG GTATTTTGTC | 350 |
| AGGCGATTGG CTTCGGTTTA AGGCACTTTC GGACCTTTAT CGGCAGGCCG | 400 |
| GCCAACAAGC ANGGTATTCA CCGAACGATC TGAAAGTAGG AGTGACAGGG | 450 |
| CATGCGTTTA TTGGAAAGAC GTCGCAGCAG GCACTCAATG ACTATTACCC | 500 |
| CTATCACGCG AATTATTGGC TAACACTGAA CCAACAATTA GGGCAGCCGT | 550 |
| TACCCCAGCA ATACGTGAGG GAATTTAATT TATTAGCCTC CCCAGAGCAA | 600 |
| GCCTTATATG TGGGAAGCTC TCAACAAGTG GGCAGGNAAA AATTTTGCGC | 650 |
| CAACATGAGG NATTTGGTNA TAAACGTTTT ATCGCACAGA TCGACATTGG | 700 |
| CGGAATGCCC TTTAAAACAG TGGCCAAGAA TATTGAGCGG TTAGGCCACT | 750 |
| GAGGTTGCAC CTGTCGTACG AAGAGCAACA AGAGGGTAAT GGTAATAATC | 800 |
| TATTTAACTG TTTATTAGAA AACTTGGTAT CTGTTTAATT AAATAACAGG | 850 |
| AGCCTGGAAG TGGGCCAAGG CTCCTTTCTA GGGAAACCTT TTTCTATTTA | 900 |
| TATAGGCGTT GTTGCCTAAG GCTAAAGTAG GATTTTATTA AAAATATAGG | 950 |
| AATTGCTCTT TTATTCGACA CAATTATTCA ATGGAATACG ATAAATGGA | 1000 |
| GAGTGTATGT AAGCGTTATA TTTTATTGGG GGGCTGATAG AAGAAAAGGG | 1050 |
| ATGCGACAGG GTCTATTAGC TAGTTTGGTA TTCGATTTCA GATCAATGCA | 1100 |
| ACGTACGAGT TTTTTATTGA CTGCTTTGTG CAAGCGATTG CATTGAAACA | 1150 |
| AAGGAGGACA TT ATG GCT AAA AAA CTA ATT TAT GTG TGT | 1189 |
|               Met Ala Lys Lys Leu Ile Tyr Val Cys | |
|                      -25 | |

| | |
|---|---:|
| TTA AGT GTT TGT TTA GTG TTG ACC TGG GCT TTT AAT GTA | 1228 |
| Leu Ser Val Cys Leu Val Leu Thr Trp Ala Phe Asn Val | |
| -20              -15                -10 | |

| | |
|---|---:|
| AAA GGG CAA TCT GCT CAT GCT GAT GGG AAC ACG ACA ACG | 1267 |
| Lys Gly Gln Ser Ala His Ala Asp Gly Asn Thr Thr Thr | |
|       -5                -1 +1              5 | |

| | |
|---|---:|
| ATC ATT GTC CAC TAT TTT TGC CCT GCT GGT GAT TAT CAA | 1306 |
| Ile Ile Val His Tyr Phe Cys Pro Ala Gly Asp Tyr Gln | |
|          10                    15 | |

| | |
|---|---:|
| CCT TGG AGT CTA TGG ATG TGG CCA AAA GAC GGA GGT GGG | 1345 |
| Pro Trp Ser Leu Trp Met Trp Pro Lys Asp Gly Gly Gly | |
| 20                25                   30 | |

| | |
|---|---:|
| GCT GAA TAC GAT TTC AAT CAA CCG GCT GAC TCT TTT GGA | 1384 |
| Ala Glu Tyr Asp Phe Asn Gln Pro Ala Asp Ser Phe Gly | |
|          35                    40                45 | |

| | |
|---|---:|
| GCT GTT GCA AGT GCT GAT ATT CCA GGA AAC CCA AGT CAG | 1423 |
| Ala Val Ala Ser Ala Asp Ile Pro Gly Asn Pro Ser Gln | |
|             50                    55 | |

*FIG. 5A*

```
GTA GGA ATT ATC GTT CGC ACT CAA GAT TGG ACC AAA GAT              1462
Val Gly Ile Ile Val Arg Thr Gln Asp Trp Thr Lys Asp
         60              65              70

GTG AGC GCT GAC CGC TAC ATA GAT TTA AGC AAA GGA AAT              1501
Val Ser Ala Asp Arg Tyr Ile Asp Leu Ser Lys Gly Asn
             75              80

GAG GTG TGG CTT GTA GAA GGA AAC AGC CAA ATT TTT TAT              1540
Glu Val Trp Leu Val Glu Gly Asn Ser Gln Ile Phe Tyr
 85              90              95

AAT GAA AAA GAT GCT GAG GAT GCA GCT AAA CCC GCT GTA              1579
Asn Glu Lys Asp Ala Glu Asp Ala Ala Lys Pro Ala Val
         100             105             110

AGC AAC GCT TAT TTA GAT GCT TCA AAC CAG GTG CTG GTT              1618
Ser Asn Ala Tyr Leu Asp Ala Ser Asn Gln Val Leu Val
                 115             120

AAA CTT AGC CAG CCG TTA ACT CTT GGG GAA GGN NNA AGC              1657
Lys Leu Ser Gln Pro Leu Thr Leu Gly Glu Gly Xaa Ser
         125             130             135

GGC TTT ACG GTT CAT GAC GAC ACA GCA AAT AAG GAT ATT              1696
Gly Phe Thr Val His Asp Asp Thr Ala Asn Lys Asp Ile
                 140             145

CCA GTG ACA TCT GTG AAG GAT GCA AGT CTT GGT CAA GAT              1735
Pro Val Thr Ser Val Lys Asp Ala Ser Leu Gly Gln Asp
150             155             160

GTA ACC GCT GTT TTG GCA GGT ACC TTC CAA CAT ATT TTT              1774
Val Thr Ala Val Leu Ala Gly Thr Phe Gln His Ile Phe
         165             170             175

GGA GGT TCC GAT TGG GCA CCT GAT AAT CAC AGT ACT TTA              1813
Gly Gly Ser Asp Trp Ala Pro Asp Asn His Ser Thr Leu
                 180             185

TTA AAA AAG GTG ACT AAC AAT CTC TAT CAA TTC TCA GGA              1852
Leu Lys Lys Val Thr Asn Asn Leu Tyr Gln Phe Ser Gly
         190             195             200

GAT CTT CCT GAA GGA AAC TAC CAA TAT AAA GTG GCT TTA              1891
Asp Leu Pro Glu Gly Asn Tyr Gln Tyr Lys Val Ala Leu
                 205             210

AAT GAT AGC TGG AAT AAT CCG AGT TAC CCA TCT GAC AAC              1930
Asn Asp Ser Trp Asn Asn Pro Ser Tyr Pro Ser Asp Asn
215             220             225
```

*FIG. 5B*

| | | | | | | | | | | | | |
|---|---|---|---|---|---|---|---|---|---|---|---|---|
| ATT | AAT | TTA | ACA | GTC | CCT | GCC | GGC | GGT | GCA | CAC | GTC | ACT | 1969 |
| Ile | Asn | Leu | Thr | Val | Pro | Ala | Gly | Gly | Ala | His | Val | Thr |
| | | 230 | | | | 235 | | | | | 240 | |

TTT TCG TAT ATT CCG TCC ACT CAT GCA GTC TAT GAC ACA    2008
Phe Ser Tyr Ile Pro Ser Thr His Ala Val Tyr Asp Thr
            245                 250

ATT AAT AAT CCT AAT GCG GAT TTA CAA GTA GAA AGC GGG    2047
Ile Asn Asn Pro Asn Ala Asp Leu Gln Val Glu Ser Gly
    255             260             265

GTT AAA ACG GAT CTC GTG ACG GTT ACT CTA GGG GAA GAT    2086
Val Lys Thr Asp Leu Val Thr Val Thr Leu Gly Glu Asp
        270             275

CCA GAT GTG AGC CAT ACT CTG TCC ATT CAA ACA GAT GGC    2125
Pro Asp Val Ser His Thr Leu Ser Ile Gln Thr Asp Gly
280             285             290

TAT CAG GCA AAG CAG GTG ATA CCT CGT AAT GTG CTT AAT    2164
Tyr Gln Ala Lys Gln Val Ile Pro Arg Asn Val Leu Asn
        295             300             305

TCA TCA CAG TAC TAC TAT TCA GGA GAT GAT CTT GGG AAT    2203
Ser Ser Gln Tyr Tyr Tyr Ser Gly Asp Asp Leu Gly Asn
            310             315

ACC TAT ACA CAG AAA GCA ACA ACC TTT AAA GTC TGG GCA    2242
Thr Tyr Thr Gln Lys Ala Thr Thr Phe Lys Val Trp Ala
    320             325             330

CCA ACT TCT ACT CAA GTA AAT GTT CTT CTT TAT GAC AGT    2281
Pro Thr Ser Thr Gln Val Asn Val Leu Leu Tyr Asp Ser
            335             340

GCA ACG GGT TCT GTA ACA AAA ATC GTA CCT ATG ACG GCA    2320
Ala Thr Gly Ser Val Thr Lys Ile Val Pro Met Thr Ala
345             350             355

TCG GGC CAT GGT GTG TGG GAA GCA ACG GTT AAT CAA AAC    2359
Ser Gly His Gly Val Trp Glu Ala Thr Val Asn Gln Asn
            360             365             370

CTT GAA AAT TGG TAT TAC ATG TAT GAG GTA ACA GGC CAA    2398
Leu Glu Asn Trp Tyr Tyr Met Tyr Glu Val Thr Gly Gln
            375             380

GGC TCT ACC CGA ACG GCT GTT GAT CCT TAT GCA ACT GCG    2437
Gly Ser Thr Arg Thr Ala Val Asp Pro Tyr Ala Thr Ala
385             390             395

*FIG. 5C*

| | |
|---|---|
| ATT GCA CCA AAT GGA ACG AGA GGC ATG ATT GTG GAC CTG<br>Ile Ala Pro Asn Gly Thr Arg Gly Met Ile Val Asp Leu<br>400 405 | 2476 |
| GCT AAA ACA GAT CCT GCT GGC TGG AAC AGT GAT AAA CAT<br>Ala Lys Thr Asp Pro Ala Gly Trp Asn Ser Asp Lys His<br>410 415 420 | 2515 |
| ATT ACG CCA AAG AAT ATA GAA GAT GAG GTC ATC TAT GAA<br>Ile Thr Pro Lys Asn Ile Glu Asp Glu Val Ile Tyr Glu<br>425 430 435 | 2554 |
| ATG GAT GTC CGT GAC TTT TCC ATT GAC CCT AAT TCG GGT<br>Met Asp Val Arg Asp Phe Ser Ile Asp Pro Asn Ser Gly<br>440 445 | 2593 |
| ATG AAA AAT AAA GGG AAG TAT TTG GCT CTT ACA GAA AAA<br>Met Lys Asn Lys Gly Lys Tyr Leu Ala Leu Thr Glu Lys<br>450 455 460 | 2632 |
| GGA ACA AAG GGC CCT GAC AAC GTA AAG ACG GGG ATA GAT<br>Gly Thr Lys Gly Pro Asp Asn Val Lys Thr Gly Ile Asp<br>465 470 | 2671 |
| TCC TTA AAA CAA CTT GGG ATT ACT CAT GTT CAG CTT ATG<br>Ser Leu Lys Gln Leu Gly Ile Thr His Val Gln Leu Met<br>475 480 485 | 2710 |
| CCT GTT TTC GCA TCT AAC AGT GTC GAT GAA ACT GAT CCA<br>Pro Val Phe Ala Ser Asn Ser Val Asp Glu Thr Asp Pro<br>490 495 500 | 2749 |
| ACC CAA GAT AAT TGG GGT TAT GAC CCT CGC AAC TAT GAT<br>Thr Gln Asp Asn Trp Gly Tyr Asp Pro Arg Asn Tyr Asp<br>505 510 | 2788 |
| GTT CCT GAA GGG CAG TAT GCT ACA AAT GCG AAT GGT AAT<br>Val Pro Glu Gly Gln Tyr Ala Thr Asn Ala Asn Gly Asn<br>515 520 525 | 2827 |
| GCT CGT ATA AAA GAG TTT AAG GAA ATG GTT CTT TCA CTC<br>Ala Arg Ile Lys Glu Phe Lys Glu Met Val Leu Ser Leu<br>530 535 | 2866 |
| CAT CGT GAA CAC ATT GGG GTT AAC ATG GAT GTT GTC TAT<br>His Arg Glu His Ile Gly Val Asn Met Asp Val Val Tyr<br>540 545 550 | 2905 |
| AAT CAT ACC TTT GCC ACG CAA ATC TCT GAC TTC GAT AAA<br>Asn His Thr Phe Ala Thr Gln Ile Ser Asp Phe Asp Lys<br>555 560 565 | 2944 |

*FIG. 5D*

| | |
|---|---|
| ATT GTA CCA GAA TAT TAT TAC CGT ACG ATG ATG CAG GTA<br>Ile Val Pro Glu Tyr Tyr Tyr Arg Thr Met Met Gln Val<br>570 575 | 2983 |
| ATT ATA CCA ACG GAT CAG GTA CTG GAA ATG AAA TTG CAN<br>Ile Ile Pro Thr Asp Gln Val Leu Glu Met Lys Leu Xaa<br>580 585 590 | 3022 |
| GCN GAA AGG CCA ATG GTT CAA AAA TTT ATT ATT GAT TCC<br>Ala Glu Arg Pro Met Val Gln Lys Phe Ile Ile Asp Ser<br>595 600 | 3061 |
| CTT AAG TAT TGG GTC AAT GAG TAT CAT ATT GAC GGC TTC<br>Leu Lys Tyr Trp Val Asn Glu Tyr His Ile Asp Gly Phe<br>605 610 615 | 3100 |
| CGT TTT GAC TTA ATG GCG CTG CTT GGA AAA GAC ACG ATG<br>Arg Phe Asp Leu Met Ala Leu Leu Gly Lys Asp Thr Met<br>620 625 630 | 3139 |
| TCC AAA GCT GCC TCG GAG CTT CAT GCT ATT AAT CCA GGA<br>Ser Lys Ala Ala Ser Glu Leu His Ala Ile Asn Pro Gly<br>635 640 | 3178 |
| ATT GCA CTT TAC GGT GAG CCA TGG ACG GGT GGA ACC TCT<br>Ile Ala Leu Tyr Gly Glu Pro Trp Thr Gly Gly Thr Ser<br>645 650 655 | 3217 |
| GCA CTG CCA GAT GAT CAG CTT CTG ACA AAA GGA GCT CAA<br>Ala Leu Pro Asp Asp Gln Leu Leu Thr Lys Gly Ala Gln<br>660 665 | 3256 |
| AAA GGC ATG GGA GTA GCG GTG TTT AAT GAC AAT TTA CGA<br>Lys Gly Met Gly Val Ala Val Phe Asn Asp Asn Leu Arg<br>670 675 680 | 3295 |
| AAC GCG TTG GAC GGC AAT GTC TTT GAT TCT TCC GCT CAA<br>Asn Ala Leu Asp Gly Asn Val Phe Asp Ser Ser Ala Gln<br>685 690 695 | 3334 |
| GGT TTT GCG ACA GGT GCA ACA GGC TTA ACT GAT GCA ATT<br>Gly Phe Ala Thr Gly Ala Thr Gly Leu Thr Asp Ala Ile<br>700 705 | 3373 |
| AAG AAT GGC GTT GAG GGG AGT ATT AAT GAC TTT ACC TCT<br>Lys Asn Gly Val Glu Gly Ser Ile Asn Asp Phe Thr Ser<br>710 715 720 | 3412 |
| TCA CCA GGT GAG ACA ATT AAC TAT GTC ACA AGT CAT GAT<br>Ser Pro Gly Glu Thr Ile Asn Tyr Val Thr Ser His Asp<br>725 730 | 3451 |

*FIG. 5E*

```
AAC TAC ACC CTT TGG GAC AAA ATA GCC CTA AGC AAT CCT            3490
Asn Tyr Thr Leu Trp Asp Lys Ile Ala Leu Ser Asn Pro
735             740                 745

AAT GAT TCC GAA GCG GAT CGG ATT AAA ATG GAT GAA CTC            3529
Asn Asp Ser Glu Ala Asp Arg Ile Lys Met Asp Glu Leu
            750             755                 760

GCA CAA GCA GTT GTT ATG ACC TCA CAA GGC GTT CCA TTC            3568
Ala Gln Ala Val Val Met Thr Ser Gln Gly Val Pro Phe
                765                 770

ATG CAA GGC GGG GAA GAA ATG CTT CGT ANA AAA GGC GGC            3607
Met Gln Gly Gly Glu Glu Met Leu Arg Xaa Lys Gly Gly
775                 780                 785

AAC GAC AAT AGT TAT AAT GCA GGC GAT GCG GTC AAT GAG            3646
Asn Asp Asn Ser Tyr Asn Ala Gly Asp Ala Val Asn Glu
            790                 795

TTT GAT TGG AGC AGG AAA GCT CAA TAT CCA GAT GTT TTC            3685
Phe Asp Trp Ser Arg Lys Ala Gln Tyr Pro Asp Val Phe
800             805                 810

AAC TAT TAT AGC GGG CTA ATC CAC CTT CGT CTT GAT CAC            3724
Asn Tyr Tyr Ser Gly Leu Ile His Leu Arg Leu Asp His
            815                 820                 825

CCA GCC TTC CGC ATG ACG ACA GCT AAT GAA ATC AAT AGC            3763
Pro Ala Phe Arg Met Thr Thr Ala Asn Glu Ile Asn Ser
                830                 835

CAC CTC CAA TTC CTA AAT AGT CCA GAG AAC ACA GTG GCC            3802
His Leu Gln Phe Leu Asn Ser Pro Glu Asn Thr Val Ala
840                 845                 850

TAT GAA TTA ACT GAT CAT GTT AAT AAA GAC AAA TGG GGA            3841
Tyr Glu Leu Thr Asp His Val Asn Lys Asp Lys Trp Gly
            855                 860

AAT ATC ATT GTT GTT TAT AAC CCA AAT AAA ACT GTA GCA            3880
Asn Ile Ile Val Val Tyr Asn Pro Asn Lys Thr Val Ala
865                 870                 875

ACC ATC AAT TTG CCG AGC GGG AAA TGG GCA ATC AAT GCT            3919
Thr Ile Asn Leu Pro Ser Gly Lys Trp Ala Ile Asn Ala
            880                 885                 890

ACG AGC GGT AAG GTA GGA GAA TCC ACC CTT GGT CAA GCA            3958
Thr Ser Gly Lys Val Gly Glu Ser Thr Leu Gly Gln Ala
                895                 900
```

*FIG. 5F*

```
GAG GGA AGT GTC CAA GTA CCA GGT ATA TCT ATG ATG ATC              3997
Glu Gly Ser Val Gln Val Pro Gly Ile Ser Met Met Ile
    905             910             915

CTT CAT CAA GAG GTA AGC CCA GAC CAC GGT AAA AAG TAATAGAAAA       4043
Leu His Gln Glu Val Ser Pro Asp His Gly Lys Lys
        920             925

AAGTAAAATC CCCTCAAGAT GTTTGAGGGG GATTTAGTTA CTTATTATCC            4093
AATTAATTTG CGGCTTCGGT GTTTTCAATG GGCTCCGTAT CCGTTCGGTT            4143
GTGTGATCGG ACAAATGGGA GTGAATAGGT CACAAGAGCA GCAGCCATTT            4193
CAAGCAGACC AGCGAAAGTA AACATTCGTT CTGGTGCAAA TCGGGTCATC            4243
AACCAACCGG TAATTGCTTG GGAAATAGGG ATGGACCCTG ACATCACGAT            4293
AATCATAATA CTAATAACAC GACCGAATAA CTAGGTGGA ATAAGCGTAT             4343
GGTTAACGCT TGGAGCAATA ATATTAACCG CCGTTTCATG AGCGCCAACA            4393
AGCACTAGAA GGGCTAAAAT AACCCATAAG TTGTGTGTAA ATCCTATAAA            4443
AAATAACATA AGGCCCTGCA G                                           4464
```

FIG. 5G

PROCESS FOR THE PRODUCTION OF NOVEL PULLULANASE

This is a divisional of application Ser. No. 08/174,893, filed Dec. 28, 1993 now abandoned.

The invention relates to a new pullulanase. The invention also relates to a new strain of microorganisms which produce this pullulanase and the processes for the preparation of this pullulanase. The invention also relates to uses thereof and compositions comprising this product. The invention also relates to a DNA molecule containing the gene of this pullulanase and to an expression vector containing this DNA molecule, which can be used to express pullulanase in Bacillus strains.

Starch, the essential constituents of which are amylose and amylopectin, can be converted into simple sugars by an enzymatic process carried out in two stages: one stage of liquefaction of the starch and one stage of saccharification of the liquefied starch. In order to obtain a high conversion level of the starch, it has already been proposed to add an enzyme which hydrolyses α-1,6-glucosidic bonds, such as, for example, a pullulanase, during the saccharification of the liquefied starch.

European Patent 0 063 909 describes a so-called debranching enzyme, that is to say an enzyme which is capable of hydrolysing the α-1,6-glucosidic bonds in amylopectin, which has a pullulanase activity and has an optimum activity at a pH of 4–5 at 60° C. This enzyme is derived from a strain of Bacillus acidopullulyticus.

U.S. Pat. No. 5,055,403 furthermore has proposed a pullulanase which has an enzymatic activity in an acid medium and is derived from a strain of Bacillus naganoensis. This enzyme has a maximum activity at a pH of about 5, measured at 60° C., and a maximum activity at a temperature of 62.5° C., measured at a pH of 4.5.

Although active at acid pH and at a temperature of about 60° C. and therefore suitable for use in the saccharification of liquefied starch, the pullulanases of the prior art have the disadvantage of having a very low stability under such temperature and pH conditions, their half-life at a temperature of 60° C. and at a pH of about 4.5 in the absence of substrate not exceeding a few tens of minutes.

There is consequently currently a demand for a pullulanase which can be used in the saccharification of liquefied starch and is very stable within a wide temperature and pH range, in particular at a temperature of about 60° C. and at a pH of about 4.5.

The object of the present invention is to provide a new pullulanase which is active at an acid pH, has a heat stability at an acid pH which is very greatly superior to that of the pullulanases of the prior art and has a half-life of several hours under the abovementioned conditions.

The object of the present invention is also to identify, isolate and provide a strain, and particularly a Bacillus strain, which naturally produces the said pullulanase.

The object of the present invention is also to isolate and provide a nucleotide sequence which codes for the said pullulanase.

The object of the present invention is also to prepare and provide an expression vector and a chromosomal integration vector containing the nucleotide sequence which codes for the said pullulanase.

The object of the present invention is also to prepare and provide a Bacillus host transformed with the expression vector or the integration vector containing the nucleotide sequence of the strain of Bacillus which codes for the said pullulanase.

To this effect, the invention relates to a pullulanase produced by a Bacillus, and more particularly by an aerobic and non-thermophilic microorganism, such as Bacillus deramificans. Bacillus deramificans T 89.117D or a derivative or mutant of this strain of Bacillus deramificans are preferably employed.

The isolated and purified pullulanase is preferably made up of a single type of polypeptide having a molecular weight of about 100 (±10) kDa.

Moreover, the N-terminal sequence (SEQ ID NO:1) of the said pullulanase is as follows, in the amino-carboxyl sense and from left to right:

Asp Gly Asn Thr Thr Thr Ile Ile Val His
 1                5               10
Tyr Phe Cys Pro Ala Gly Asp Tyr Gln Pro
           15              20

The invention relates to an isolated and purified pullulanase comprising the amino acid sequence of 1 to 928 amino acids (SEQ ID NO:11) or a modified sequence derived therefrom. This sequence is the complete amino acid sequence of the said pullulanase, as illustrated in FIG. 4 (4a to 4f).

The complete nucleotide sequence (SEQ ID NO:10) which codes for pullulanase and its translation into amino acids is given in FIG. 4.

Particularly preferably, the said pullulanase has an isoelectric point of between 4.1 and 4.5.

The pullulanase according to the invention is heat stable and active in a wide temperature range. The pullulanase is active at an acid pH.

The said pullulanase is capable of catalysing the hydrolysis of α-1,6-glucosidic bonds present both in amylopectin and in pullulane. It is therefore a so-called deramifying or debranching enzyme. The said pullulanase is preferably capable of hydrolysing glucosidic bonds of the α-1,6 type in amylopectin.

The pullulanase according to the invention preferably breaks down pullulane into maltotriose and amylopectin into amylose.

Moreover, the pullulanase of the present invention hydrolyses amylopectin to form oligosaccharides (maltooligosaccharides). During this hydrolysis, the formation of oligosaccharides made up of about 13 glucose units (degree of polymerization of 13, this molecule is also called "chain A") is observed, followed by the formation of oligosaccharides made up of about 47 glucose units (degree of polymerization of 47, this molecule is also called "chain B").

The oligosaccharides with chains A and B are defined with reference to D. J. MANNERS ("Structural Analysis of Starch components by Debranching Enzymes" in "New Approaches to research on Cereal Carbohydrates", Amsterdam, 1985, pages 45–54) and B. E. ENEVOLDSEN ("Aspects of the fine structure of starch" in "New Approaches to research on Cereal Carbohydrates", Amsterdam, 1985, pages 55–60).

The pullulanase of the present invention preferably hydrolyses potato amylopectin. This hydrolysis can be carried out with an aqueous suspension of amylopectin in the presence of the pullulanase under the conditions of optimum activity of the pullulanase, that is to say at a temperature of about 60° C. and at a pH of about 4.3.

The pullulanase of the present invention catalyses the condensation reaction of maltose to form tetraholosides (oligosaccharides having 4 glucose units).

The pullulanase of the invention has a half-life of about 55 hours, measured at a temperature of about 60° C. in a solution buffered at a pH of about 4.5 and in the absence of substrate.

Half-life means that the pullulanase shows a relative enzymatic activity of at least 50%, measured after an incubation of 55 hours at a temperature of about 60° C. in a solution buffered at a pH of about 4.5 and in the absence of substrate.

The pullulanase according to the invention is heat stable at an acid pH. In fact, the pullulanase according to the invention shows a relative enzymatic activity of at least 55%, measured after an incubation of 40 hours at a temperature of 60° C. in a solution buffered at a pH of about 4.5 and in the absence of substrate. It shows a relative enzymatic activity of at least 70%, measured after an incubation of 24 hours under these same conditions.

Relative enzymatic activity means the ratio between the enzymatic activity measured in the course of a test carried out under the given pH, temperature, substrate and duration conditions, and the maximum enzymatic activity measured in the course of this same test, the enzymatic activity being measured starting from the hydrolysis of pullulane and the maximum enzymatic activity being fixed arbitrarily at the value of 100.

The pullulanase according to the invention is furthermore stable in a wide range of acid pH values.

Under the conditions described below, it is active at a pH greater than or equal to 3. In fact, the said pullulanase shows a relative enzymatic activity of at least 85%, measured after an incubation of 60 minutes at a temperature of about 60° C. in the absence of substrate and in a pH range greater than or equal to about 3.5.

Under the conditions described below, it is active at a pH of less than or equal to 7. In fact, the said pullulanase shows a relative enzymatic activity of at least 85%, measured after an incubation of 60 minutes at a temperature of about 60° C. in the absence of substrate and in a pH range less than or equal to about 5.8.

It preferably shows a relative enzymatic activity of greater than 90%, measured in a pH range of between about 3.8 and about 5 under these same conditions.

The pullulanase according to the invention develops an optimum enzymatic activity, measured at a temperature of about 60° C., in a pH range greater than 4.0. The pullulanase according to the invention develops an optimum enzymatic activity, measured at a temperature of about 60° C., in a pH range less than 4.8. The said pullulanase preferably develops an optimum enzymatic activity, measured at a temperature of about 60° C., at a pH of about 4.3.

The pullulanase according to the invention furthermore develops an optimum enzymatic activity, measured at a pH of about 4.3, in a temperature range of between 55 and 65° C., and more particularly at 60° C.

The pullulanase according to the invention develops an enzymatic activity of more than 80% of the maximum enzymatic activity (the maximum enzymatic activity being measured at a temperature of 60° C. and at a pH of 4.3) in a pH range between about 3.8 and about 4.9 at a temperature of about 60° C.

The pullulanase according to the invention furthermore has all the appropriate properties compatible with actual industrial conditions of saccharification of starch. These properties are an optimum pH of less than 5, an optimum temperature at about 60° C. and a good stability of the enzyme under these conditions of acid pH and elevated temperature. The acid medium is imposed by the simultaneous use of glucoamylase and pullulanase in the industrial saccharification of starch. In fact, the glucoamylase used for saccharification of starch is generally produced by a fungus and in particular by an Aspergillus strain, such as *Aspergillus niger, Aspergillus awamori* or *Aspergillus foetidus*. The ideal conditions which are suitable for saccharification of liquefied starch in the presence of a glucoamylase are a temperature of about 60° C. and a pH of about 4.0 to 4.5. This is the case, in particular, for the glucoamylase sold under the trade names DIAZYME® L-200 by SOLVAY ENZYMES (Elkhart, United States) and OPTIDEX® by SOLVAY ENZYMES (Hanover, Germany). Furthermore, the saccharification stage lasts several hours, in general 40 to 60 hours, and it is essential that the enzymes used are stable, active and effective throughout this stage, and these enzymes should therefore have a high heat stability in an acid medium and the longest possible half-life. For this reason, the pullulanase of the present invention is more effective than the known pullulanases.

The present invention also relates to a process for the production of a pullulanase which comprises culture of an aerobic (and non-thermophilic) bacterium which is capable of producing pullulanase in a suitable nutrient medium containing sources of carbon and nitrogen and mineral salts under aerobiotic conditions, and harvesting of the pullulanase thus obtained. This culture medium may be solid or liquid. The culture medium is preferably liquid.

The present invention also relates to a process for the production of a pullulanase which comprises culture of the strain *Bacillus deramificans* T 89.117D (LMG P-13056) or a derivative of this strain which is capable of producing pullulanase in a suitable nutrient medium containing sources of carbon and nitrogen and mineral salts under aerobiotic conditions, and harvesting of the pullulanase thus obtained.

The culture conditions for these bacteria, such as the components of the culture medium, culture parameters, temperature, pH, aeration and stirring, are well-known to the expert.

The sources of carbon in the culture medium are usually chosen from starch, partially hydrolysed starch, soluble starch, oligosaccharides, glucose, amylose, amylopectin or a mixture of two or more of these. The sources of carbon in the culture medium are preferably chosen from partially hydrolysed starch, pullulane, glucose or a mixture of these. Good results have been obtained with glucose and partially hydrolysed starch. The sources of nitrogen in the culture medium are usually chosen from yeast extract, soya flour, cottonseed flour, fish meal, gelatin, potato flour or a mixture of two or more of these. The sources of nitrogen in the culture medium are preferably chosen from yeast extract, soya flour or a mixture of these. Good results have been obtained with yeast extract. The mineral salts in the culture medium are generally chosen, with respect to the anions, from chloride, carbonate, phosphate and sulphate, and, with respect to the cations, from potassium, sodium, ammonium, magnesium, calcium or a mixture of two or more of these. Good results have been obtained with a mixture of the following salts: $KH_2PO_4$, $K_2HPO_4.3H_2O$, $(NH_4)_2SO_4$, $MgCl_2.6H_2O$ and $CaCl_2.2H_2O$.

Culture is generally carried out at a temperature of between 20 and 45° C., preferably between 25 and 40° C.

Culture is generally carried out at a pH of between 3.5 and 6, preferably between 4 and 6.

Culture is carried out under aerobiotic conditions in the presence of air or oxygen and while stirring.

The techniques for harvesting the pullulanase produced are well known to the expert. Centrifugation, ultrafiltration, evaporation, precipitation, filtration, microfiltration, crystallization or a combination of one or other of these techniques, such as centrifugation followed by ultrafiltration, is usually employed.

The pullulanase can then be purified, if necessary. The techniques for purification of enzymes are known to the expert, such as, in particular, precipitation with the aid of a salt such as ammonium sulphate, or a solvent such as, chiefly, acetone.

The pullulanase can also be dried by spraying or lyophilization.

The present invention also relates to identification and provision of a new isolated aerobic bacterium which produces pullulanase. Generally, this belongs to the family of Bacillaceae. It preferably belongs to the Bacillus genus. The said Bacillus is particularly preferably the strain *Bacillus deramificans* T 89.117D or a derivative or mutant of this strain.

Derivative or mutant of this strain means any naturally or artificially modified bacterium. The derivatives of this strain can be obtained by known modification techniques, such as ultra-violet radiation, X-rays, mutagenic agents or genetic engineering.

The strain *Bacillus deramificans* T 89.117D has been deposited in the collection called BELGIAN COORDINATED COLLECTIONS OF MICROORGANISMS (LMG culture collection, University of Ghent, Laboratory of Microbiology—K. L. Ledeganckstraat 35, B-9000 GHENT, Belgium) in accordance with the Treaty of Budapest under number LMG P-13056 on 9 Dec. 1992. The invention thus relates to an isolated and purified culture of *Bacillus deramificans* T 89.117D and a derived or mutated culture thereof.

The strain of the present invention has been identified by its biochemical characteristics: a Gram-positive, aerobic, rod-shaped bacterium which forms an endospore.

The invention also relates to the isolation and provision of a DNA molecule comprising a nucleotide sequence (SEQ ID NO:10) which codes for the pullulanase of *Bacillus deramificans* T 89.117D (LMG P-13056) or a modified sequence derived therefrom. This DNA molecule preferably comprises the entire gene of the pullulanase of *Bacillus deramificans* T 89.117D. The entire gene of the pullulanase means at least the transcription promoter(s), the signal sequence(s), the nucleotide sequence which codes for the mature pullulanase and the transcription terminator(s).

The DNA molecule according to the invention comprises at least the nucleotide sequence (SEQ ID NO:10) which codes for the mature pullulanase of *Bacillus deramificans* T 89.117D (LMG P-13056) and its signal sequence (presequence) (SEQ ID NO:13). This DNA molecule preferably comprises the entire gene of the pullulanase of *Bacillus deramificans* T 89.117D. Good results have been obtained with a DNA molecule comprising the nucleotide sequence (SEQ ID NO:8). The nucleotide sequence (SEQ ID NO:8) is made up of, in the amino-carboxyl sense and from left to right, the nucleotide sequence (SEQ ID NO:14), the nucleotide sequence (SEQ ID NO:13), the nucleotide sequence (SEQ ID NO:10) and the nucleotide sequence (SEQ ID NO:15).

The pullulanase of the invention is synthesized in the form of a precursor containing an additional sequence of 29 amino acids (SEQ ID NO:12).

The invention also relates to a modified pullulanase, that is to say an enzyme in which the amino acid sequence differs from that of the wild enzyme by at least one amino acid. These modifications can be obtained by the conventional techniques of mutagenesis on DNA, such as exposure to ultra-violet radiation, or to chemical products, such as sodium nitrite or O-methylhydroxylamine, or by genetic-engineering techniques, such as, for example, site-directed mutagenesis or random mutagenesis.

The invention also relates to a mutated pullulanase obtained by modification of the nucleotide sequence of the gene which codes for the pullulanase defined above. The techniques for obtaining such mutated pullulanases are known to the expert and are described in particular in Molecular Cloning—a laboratory manual—SAMBROOK, FRITSCH, MANIATIS—second edition, 1989, in chapter 15.

The invention also relates to the preparation and provision of an expression vector containing the DNA molecule which comprises the nucleotide sequence which codes for the pullulanase of *Bacillus deramificans* T 89.117D. The DNA molecule preferably comprises the structural gene which codes for the mature pullulanase of *Bacillus deramificans* T 89.117D. This vector is particularly preferably the vector pUBDEBRA1. Good results have also been obtained with the vector pUBCDEBRA11.

Expression vector means any DNA sequence which comprises a replicon and other DNA regions (nucleotide sequences) and which functions independently of the host as a complete gene expression unit.

Complete gene expression unit means the structural gene and the promoter region(s) and the regulation region(s) necessary for transcription and translation. Structural gene means the coding sequence which is used for transcription into RNA and allows synthesis of the protein by the host.

The preferred expression vector is the vector pUBDEBRA1. This vector contains the gene which codes for the pullulanase of the strain *Bacillus deramificans* T 89.117D according to the invention. This vector can be introduced into a suitable host. This host is generally a strain of Bacillus. This host is preferably a strain of *Bacillus licheniformis*. This host is particularly preferably a strain of *Bacillus licheniformis* SE2. Excellent results have been obtained with this vector when it is introduced into the strain *Bacillus licheniformis* SE2 delap1, used as the host.

The invention also related to the preparation and provision of a chromosomal integration vector containing the DNA molecule which comprises the nucleotide sequence which codes for the pullulanase of *Bacillus deramificans* T 89.117D. The DNA molecule preferably comprises the structural gene which codes for the mature pullulanase of *Bacillus deramificans* T 89.117D. This chromosomal integration vector is particularly preferably the vector pUBCDEBRA11DNSI.

The present invention also relates to recombinant strains in which the said gene which codes for pullulanase is introduced by genetic-engineering techniques. The gene can be introduced on a plasmid by an expression vector or integrated into the host chromosome in one or more copies by a chromosomal integration vector.

The invention also relates to the strains of microorganisms which are different from the starting producer organism and in which the nucleotides which code for the pullulanase are introduced by transformation, either in a form integrated in the chromosomal DNA or in autoreplicative form (plasmid).

The invention relates to the transformed strain of *Bacillus licheniformis* which comprises the DNA molecule described above. The invention relates to the transformed strain of *Bacillus licheniformis* which comprises the expression vector or the chromosomal integration vector which comprises this DNA molecule. The invention preferably relates to the transformed strain of *Bacillus licheniformis* which comprises the expression vector pUBDEBRA1 or the chromosomal integration vector pUBCDEBPA11DNSI.

The invention also relates to a process for the preparation of a pullulanase starting from a recombinant organism, the process comprising isolation of a DNA fragment which codes for pullulanase, insertion of this DNA fragment into a suitable vector, introduction of this vector into a suitable host or introduction of this DNA fragment into the chromosome of a suitable host, culture of this host, expression of the pullulanase and harvesting of the pullulanase. The suitable host is generally chosen from the group comprising *Escherichia coli*, Bacillus or Aspergillus microorganisms. The host is usually chosen from the Bacilli. The host is preferably chosen from (aerobic) microorganisms of the genus Bacillus. The host is particularly preferably chosen from the microorganisms *Bacillus subtilis*, *Bacillus licheniformis*, *Bacillus alcalophilus*, *Bacillus pumilus*, *Bacillus lentus*, *Bacillus amyloliquefaciens* or *Bacillus deramificans* T 89.117D (LMG P-13056).

Good results have been obtained when the host for expression of the pullulanase according to the present invention is a recombinant strain derived from *Bacillus licheniformis*, and preferably the strain *Bacillus licheniformis* SE2 delap1.

The strain of Bacillus licheniformisSE2 was deposited on 21 Jun. 1993 in the collection called BELGIAN COORDINATED COLLECTIONS OF MICROORGANISMS (LMG culture collection, Ghent, Belgium) in accordance with the Treaty of Budapest under number LMG P-14034.

The transformed strain SE2 delap1 thus obtained from *Bacillus licheniformis* SE2 differs from the parent strain by the sole fact that it does not contain in its chromosome the DNA sequence which codes for the mature protease.

The invention also relates to a pullulanase produced in a heterologous manner by a microorganism of the genus Bacillus which contains a gene which codes for an alkaline protease in the wild state. This microorganism is preferably a strain of *Bacillus licheniformis* comprising the DNA molecule which comprises the nucleotide sequence which codes for the pullulanase of *Bacillus deramificans* T 89.117D. The gene which codes for the alkaline protease has particularly preferably been deleted from this strain of Bacillus. This strain is preferably the strain *Bacillus licheniformis* SE2 delap1.

Produced in a heterologous manner means production which is not effected by the natural microorganism, that is to say the microorganism which contains, in the wild state, the gene which codes for the pullulanase.

The pullulanase according to the invention has several outlets in various industries, such as, for example, the food industry, the pharmaceuticals industry or the chemical industry.

The pullulanase can in particular be used in baking as an "anti-staling" agent, that is to say as an additive to prevent bread becoming stale during storage, or in brewing during production of low-calorie beers.

The pullulanase can also be used in the preparation of low-calorie foods in which amylose is used as a substitute for fats.

The pullulanase can also be used to hydrolyse amylopectin and to form oligosaccharides starting from this amylopectin.

The pullulanase can also be used to form tetraholosides starting from maltose.

The pullulanase can also be used to condense mono- or oligo-saccharides, creating bonds of the alpha-1,6 type.

The pullulanase can be used, for example, to clarify fruit juices.

The pullulanase can be used for liquefaction of starch.

For food applications, the pullulanase can be immobilized on a support. The techniques for immobilization of enzymes are well known to the expert.

The pullulanase according to the invention is particularly suitable for treatment of starch and pullulane.

The invention relates to the use of the pullulanase for saccharification of liquefied starch.

The present invention also relates to the use of the pullulanase in a process for breaking down starch or partially hydrolysed starch comprising a stage of saccharification of the starch or the partially hydrolysed starch in the presence of a pullulanase. This process is in general carried out in the presence of one or more other enzymes, such as glucoamylase, α-amylase, β-amylase, α-glucosidase or other saccharifying enzymes.

Given its biochemical properties, the pullulanase according to the present invention allows the saccharification stage to be carried out under strongly acid conditions, that is to say down to a pH of at least 3.9. This pH is more acid than that which is acceptable to the known pullulanases.

Given its biochemical properties, the pullulanase according to the present invention allows the saccharification stage to be carried out at relatively high temperatures, that is to say up to at least a temperature of 65° C.

Addition of the pullulanase according to the present invention to the saccharification medium allows the content of glucose in the final composition obtained to be increased and therefore the yield of the reaction to be increased.

Moreover, addition of the pullulanase of the present invention to the saccharification medium allows the saccharification period to be reduced.

The pullulanase of the present invention allows a high starch conversion level to be achieved.

Furthermore, during the saccharification stage, it is possible for a large proportion (at least 60%) of the glucoamylase usually used to be replaced by the pullulanase of the present invention without affecting the yield of glucose. This replacement is particularly advantageous, and in fact it allows the amount of by-products usually obtained to be reduced considerably. Since the glucoamylase is present in a small proportion, it is unable to catalyse the synthesis reaction of oligosaccharides (containing α-1,6 bonds) starting from glucose; under the normal conditions, glucoamylase catalyses this inverse reaction of oligosaccharide synthesis when high concentrations of dextrose are reached in the saccharification medium, which limits the starch conversion level.

Furthermore, the pullulanase of the present invention allows a concentrated saccharification medium, that is to say a medium having a high content of liquefied starch, to be used. This is advantageous from the economic point of view, and in fact allows the evaporation costs to be reduced.

The present invention also relates to enzymatic compositions comprising the pullulanase according to the invention.

The compositions comprising the pullulanase of the present invention can be used in the solid or liquid form.

The pullulanase is formulated according to the intended uses. Stabilizers or preservatives can also be added to the enzymatic compositions comprising the pullulanase according to the invention. For example, the pullulanase can be stabilized by addition of propylene glycol, ethylene glycol, glycerol, starch, pullulane, a sugar, such as glucose and sorbitol, a salt, such as sodium chloride, calcium chloride, potassium sorbate and sodium benzoate, or a mixture of two or more of these products. Good results have been obtained with propylene glycol. Good results have been obtained with a mixture of starch, sodium benzoate and potassium sorbate.

The enzymatic compositions according to the invention can also comprise, in addition to the pullulanase, one or more other enzymes. Such enzymes are, in particular, carbohydrate hydrolases, such as, for example, glucoamylase, α-amylase, β-amylase, α-glucosidase, isoamylase, cyclomaltodextrin glucotransferase, β-glucanase and glucose isomerase, saccharifying enzymes, enzymes which cleave glucosidic bonds or a mixture of two or more of these.

The present invention preferably relates to an enzymatic composition comprising a glucoamylase and a pullulanase.

FIG. 4 (FIGS. 4a to 4f) shows the nucleotide sequence (SEQ ID NO:10) which codes for the mature pullulanase, and its translation into amino acids (SEQ ID NO:11).

FIG. 5 (FIGS. 5a to 5g) shows the nucleotide sequence (SEQ ID NO:8) of the DNA fragment from the BamHI site to the PstI site of the plasmid pUBCDEBRA11, and the translation into amino acids (SEQ ID NO:9) of signal and mature sequences of the pullulanase. The nucleotides which have not been determined with certainty have been shown by the symbol N.

Figure 1:
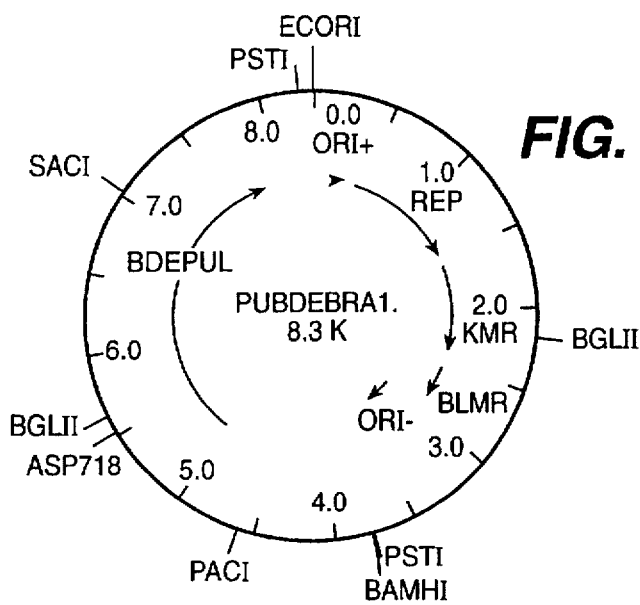
FIG. 1 shows the restriction map of the plasmid pUBDEBRA1.

The meaning of the symbols and abbreviations used in these figures is summarized in the following table.

| Symbol Abbreviation | Meaning |
| --- | --- |
| ORIEC | Replication origin in *E. coli* |
| REP | Protein required for replication |
| ORI+ | Replication origin of the + strand |
| ORI– | Replication origin of the – strand |
| KMR | Gene carrying resistance to kanamycin |
| BLMR | Gene carrying resistance to bleomycin |
| AMPR | Gene carrying resistance to amplicillin |
| PP | Pre/pro sequence |
| BLIAPR | Sequence which codes for the alkaline protease of *B. licheniformis* |
| 5'BLIAPR | 5' sequence situated before the sequence which codes for the alkaline protease of *B. licheniformis* |
| 3'BLIAPR | 3' sequence situated after the sequence which codes for the alkaline protease of *B. licheniformis* |
| BDEPUL | Sequence which codes for the pullulanase of *B. deramificans* |

The present invention is illustrated by the following examples.

EXAMPLE 1

Isolation and Characterization of the Strain of *Bacillus deramificans*

The strain *Bacillus deramificans* T 89.117D was isolated from soil on an agar-agar nutrient medium and selected for its ability to break down a coloured derivative of pullulane known by the name AZCL-pullulane and sold by the company MEGAZYME.

This strain was cultured at 37° C. in MYE growth medium, the composition of which is as follows: $KH_2PO_4$ 33 mM; $K_2HPO_4.2H_2O$ 6 mM; $(NH_4)_2SO_4$ 45 mM; $MgCl_2.6H_2O$ 1 mM; $CaCl_2.2H_2O$ 1 mM; yeast extract 0.5% (weight/volume); glucose 0.5% (weight/volume). The pH of the medium is adjusted to pH 4.5 with $H_3PO_4$.

The agar-agar medium (MYE/agar) additionally comprises 2% (weight/volume) of agar.

The strain of the present invention was identified by its biochemical characteristics: Gram-positive, aerobic, rod-shaped bacterium which forms an endospore. It thus belongs to the Bacillus genus.

The vegetative cells of this strain in a culture on MYE medium at 37° C. have the form of a bacillus of size 0.7×3.0–3.5 μm. The motility of the vegetative cells is low.

After growth for three days at 37° C. on the MYE medium, microscopic observation reveals the presence of slightly deformed and elliptical (sub)terminal sporangia.

The catalase test is weakly positive in the presence of 10% of hydrogen peroxide. The oxidase test is positive in the presence of 1% of tetramethyl-1,4-phenylenediammonium dichloride.

This strain is aerobic, that is to say it develops under aerobiosis. It does not develop under anaerobiosis, that is to say under an atmosphere of 84% (v/v) of $N_2$, 8% (v/v) of $CO_2$ and 8% (v/v) of $H_2$ at 37° C., but on the other hand it develops under microanaerobiosis, that is to say under an atmosphere of 82.5% (v/v) of $N_2$, 6% (v/v) of $O_2$, 7.5% (v/v) of $H_2$ and 4% (v/v) of $CO_2$ at 37° C. The abbreviation % (v/v) represents a percentage expressed as volume per volume.

This strain is not thermophilic. It shows normal development after incubation in MYE medium at 20° C., 30° C., 37° C. and 45° C., but on the other hand it does not develop at 50° C. and 55° C. It shows normal development after incubation in MYE medium buffered with phosphate buffer to the following pH values: pH 4.0, pH 4.5, pH 5.0 and pH 5.5, but on the other hand it does not develop at pH 7.0. It shows normal development after incubation in MYE medium in the presence of NaCl at concentrations of 2.0% (w/v) and 3.5% (w/v), shows weak development in the presence of 5.0% (w/v) of NaCl and does not develop in the presence of 7.0% (w/v) of NaCl. The abbreviation % (w/v) represents a percentage expressed as weight per volume.

This strain does not hydrolyse casein: in fact, no lysis zone could be observed after more than 2 weeks of incubation at 37° C. It decomposes tyrosine slightly, does not produce acetone from pyruvate and does not reduce nitrate to nitrite or to $N_2$.

The strain *Bacillus deramificans* T 89.117D according to the invention is taxonomically different from the strain of *Bacillus acidopullulyticus* described in European Patent 0 063 909 and from the strain of *Bacillus naganoensis* described in U.S. Pat. No. 5,055,403. The strain *Bacillus deramificans* T 89.117D shows growth at a pH of between 4.7 and 5.5, shows no growth at a pH of 7.0, develops in the presence of 3.5% (w/v) of NaCl, decomposes tyrosine and does not reduce nitrate to nitrite.

The strain *Bacillus deramificans* T 89.117D has been deposited in the collection called the BELGIAN COORDINATED COLLECTIONS OF MICROORGANISMS (LMG culture collection) under number LMG P-13056.

EXAMPLE 2

Preparation of Pullulanase

The strain *Bacillus deramificans* T 89.117D is cultured in a liquid medium (MYA), the composition of which is identical to that of the MYE medium except that the content of yeast extract and glucose is replaced by starch, that is to say: Yeast extract 2.5% (w/v) Potato starch 2.5% (w/v).

The culture is carried out while stirring, with effective aeration, at a temperature of 37° C.

After 68 hours of culture, the pullulanase and the cell biomass are separated by centrifugation (5000 revolutions per minute for 30 minutes, BECKMAN JA-10). The pullulanase produced by the strain *Bacillus deramificans* T 89.117D is extracellular.

The pullulanase is then concentrated by ultrafiltration (AMICON S10 Y10 membrane) to obtain a concentrated aqueous solution of pullulanase.

The enzymatic activity of the solution obtained is measured.

One enzymatic unit of pullulanase (PUN) is defined as the amount of enzyme which, at a pH of 4.5, at a temperature of 60° C. and in the presence of pullulane, catalyses the release of reducing sugars at a rate of 1 μM glucose equivalent per minute.

The pullulanase enzymatic activity is measured in accordance with the following protocol. 1 ml of a 1% strength solution of pullulane in a 50 mM acetate buffer at pH 4.5 is incubated at 60° C. for 10 minutes. 0.1 ml of a solution of pullulanase corresponding to an activity of between 0.2 and 1 PUN/ml is added thereto. The reaction is stopped after 15 minutes by addition of 0.4 ml of 0.5M NaOH. The reducing sugars released are analysed by the method of SOMOGYI-NELSON [J. Biol. Chem., 153 (1944) pages 375–380; and J. Biol. Chem., 160 (1945), pages 61–68], and as in the other examples of this Application.

A second method is used to analyse the pullulanase. The enzymatic reaction in the presence of pullulane is carried out in accordance with the test conditions, and is then stopped by addition of sulphuric acid (0.1N). The hydrolysis products of pullulane are then subjected to HPLC chromatography (HPX-87H column from BIO-RAD; the mobile phase is 10 mM $H_2SO_4$) in order to separate the various constituents. The amount of maltotriose formed is estimated by measurement of the area of the peak obtained.

The so-called debranching activity, that is to say the hydrolysis of the α-1,6-glucosidic bonds present in amylopectin, can be quantified by the increase in the blue coloration caused, in the presence of iodine, by the release of amylose from amylopectin.

The debranching enzymatic activity is measured in accordance with the following protocol. 0.4 ml of a 1% strength amylopectin solution containing a 50 mM acetate buffer at pH 4.5 is incubated at 60° C. for 10 minutes. The reaction is initiated by addition of 0.2 ml of pullulanase, and is stopped after 30 minutes by addition of 0.4 ml of 0.3M HCl. 0.8 ml of a 0.0025% (v/v) strength solution of iodine is then added to 0.2 ml of this reaction mixture and the optical density is measured at 565 nm.

In order to purify the pullulanase, the aqueous concentrated solution of pullulanase is diafiltered by 6 portions of 500 ml of an aqueous solution of 9 g/l of NaCl, and the pH of the aqueous solution thus obtained is adjusted to pH 3.5 by addition of 25% (v/v) strength HCl at room temperature. The diafiltration comprises mixing the pullulanase solution with the NaCl solution and then subjecting the solution obtained to ultrafiltration.

The precipitate obtained is removed by centrifugation (5000 revolutions per minute for 30 minutes, BECKMAN JA-10), and the supernatant from the centrifugation is collected. The pH of this supernatant is adjusted to pH 6.0 by addition of 5M NaOH. The precipitate obtained is removed by centrifugation.

The supernatant from the centrifugation is collected and is heated at 55° C. for 15 minutes.

The precipitate formed is removed again by centrifugation (5000 revolutions per minute for 30 minutes, BECKMAN JA-10). The supernatant from the centrifugation is collected.

Acetone is added to this supernatant to a final concentration of 60% (v/v), and the suspension formed is brought to 4° C. over a period of 2 hours. The precipitate formed at 4° C. is dissolved in a buffer of 20 mM MES (2-(N-morpholino)ethanesulphonic acid) and 1 mM $CaCl_2$ (pH 6.0). This pullulanase solution is called solution A.

This solution A is concentrated again by ion exchange chromatography in order to purify it. A column of about 20 ml internal volume sold under the trade name (S-SEPHAROSE® HP HI LOAD 16/10, is first equilibrated with a buffer of 50 mM $CH_3COONa$ and 100 mM NaCl (pH 4.0) at a flow rate of 5 ml/minute. Solution A is diluted 10 times in the acetate buffer and 15 ml of this dilute solution are deposited on the column. An isocratic phase is ensured by elution of 80 ml of acetate buffer (100 mM NaCl), followed by elution by 200 ml of 50 acetate buffer (pH=4.0) containing a linear gradient of NaCl (100–500 mM).

The pullulanase activity is measured in each fraction.

The most active fractions are combined into a solution called B (12 ml containing 0.025 mg/ml of proteins and having a pullulanase activity of 0.7 PUN/ml).

Starting from this solution B, precipitation is effected with acetone at a final concentration of 80% v/v). The precipitate obtained is dissolved in a volume of 0.6 ml of buffer comprising 20 mM MES and 1 mM $CaCl_2$ (pH 6.0).

This pullulanase solution is called solution C.

Solution C has a protein content of 0.4 mg/ml, an enzymatic activity of 12 PUN/ml and a specific activity of 30 PUN/mg.

The results are summarized in Table 1.

TABLE 1

| Fractions | Volume ml | Proteins mg/ml | Total | % | Pullulanase activity PUN/ml | Total | % | Specific activity PUN/mg |
|---|---|---|---|---|---|---|---|---|
| Solution A | 1.5 | 6.48 | 9.7 | 100 | 17.5 | 26.3 | 100 | 2.7 |
| Solution B | 12 | 0.025 | 0.3 | 3 | 0.7 | 8.4 | 32 | 28 |

Table 1 shows that this purification stage has increased the specific pullulanase activity of the enzymatic solution by a factor of 10.

The debranching activity, that is to say the hydrolysis activity with regard to alpha-1,6 bonds in amylopectin, of the pullulanase was also measured as described above by coloration with iodine after hydrolysis of amylopectin. The results show that the debranching activity has also been increased.

EXAMPLE 3

Molecular Weight Determination

Precipitation by means of trichloroacetic acid (10% (v/v) final strength) is carried out on solution C as obtained in Example 2. The precipitate obtained is taken up in a buffer composed of 10 mM TRIS/HCl (pH=8.0), 1 mM EDTA, 2.5% (w/v) of SDS (sodium dodecyl sulphate), 5% (v/v) of β-mercaptoethanol and 0.01% (w/v) of bromophenol blue.

4 μl of the precipitate taken up in the buffer are deposited on a polyacrylamide gel. The gel system used is the PHAST-SYSTEM system from PHARMACIA LKB BIOTECHNOLOGY, with gels containing a polyacrylamide gradient of 10–15% (v/v) in the presence of SDS. The electrophoresis conditions are those prescribed by the supplier. Coloration of the gel with Coomassie blue reveals a polypeptide of molecular weight of about 105 kDaltons, which is the main component of solution C.

This is confirmed by the estimation made from the amino acid sequence of the mature form of the pullulanase (without the signal sequence), as described in Example 4, and a molecular weight of 102 KDaltons is deduced by calculation.

EXAMPLE 4

1. Determination of the N-terminal Sequence

Starting from the gel described in Example 3, the N-terminal sequence of the pullulanase is identified by following the technique described by BAUW et al., (1987), Proc. Natl. Acad. Sci. USA, 84, pages 4806–4810.

This sequence (SEQ ID NO:1) thus determined is as follows in the amino-carboxyl sense and from left to right:
Asp Gly Asn Thr Thr Thr Ile Ile Val His Tyr Phe Cys Pro Ala Gly Asp Tyr Gln Pro

2. Determination of the Amino Acid Sequence of the Pullulanase

The nucleotide sequence (SEQ ID NO:8) of the BamHI-PstI fragment of about 4.5 Kb of the plasmid pUBCDE-BRA11 containing the gene which codes for the pullulanase, as obtained in Example 21, was determined by the chain termination method using dideoxy-nucleotides of SANGER et al. (1977) Proc. Natl. Acad. Sci. USA 74, pages 5463–5467.

The synthetic oligonucleotides used to initiate the elongation reactions by the T7 DNA polymerase were synthesized by the method of BEAUCAGE et al. (1981) Tetrahedron letters 22, pages 1859–1882. The sequencing was carried out in accordance with the protocol given by the supplier of the sequence analysis kit (PHARMACIA), proceeding with denaturation of double-stranded DNA by treatment with NaOH.

The sequence analysis strategy is described by SAMBROOK, 1989, pages 13.15 and 13.17. The polyacrylamide gels for the sequence analysis were prepared in accordance with the technique described by SAMBROOK, 1989, pages 13.45–13.58.

The nucleotide sequence (SEQ ID NO:8) of the DNA fragment from the BamHI site to the PstI site of pUBCDEBPA11, and also the translation into amino acids (SEQ ID NO:9) of the signal and mature sequences of the pullulanase, was identified (FIG. 5). The nucleotides which have not been determined with certainty have been shown by the symbol N.

Analysis of this sequence shows the presence of an open reading frame which codes for the pullulanase. The nucleotide sequence which codes for the mature pullulanase (SEQ ID NO:10) is identified. The amino acid sequence of the mature pullulanase (SEQ ID NO:11) is thus deduced by translation of this open reading frame. FIG. 4 shows the nucleotide sequence which codes for the mature pullulanase and also its translation into amino acids.

It is verified that the N-terminal sequence determined experimentally from the protein as described above corresponds to that translated from the DNA sequence.

This shows that the pullulanase is synthesized in the form of a precursor containing an additional sequence of 29 amino acids (presequence). This sequence of 29 amino acids is identified (SEQ ID NO:12), as is the corresponding nucleotide sequence (SEQ ID N:13). This additional sequence shows the typical characteristics of a secretion signal sequence, which is eliminated during exportation of the enzyme to the outside of the cell (Freudl, (1992), Journal of Biotechnology, 23, pages 231–240).

This sequence of 29 amino acids is as follows:

```
ATG GCT AAA AAA CTA ATT TAT GTG TGT
Met Ala Lys Lys Leu Ile Tyr Val Cys
                                -25

TTA AGT GTT TGT TTA GTG TTG ACC TGG GCT TTT AAT GTA
Leu Ser Val Cys Leu Val Leu Thr Trp Ala Phe Asn Val
-20              -15                      -10

AAA GGG CAA TCT GCT CAT GCT
Lys Gly Gln Ser Ala His Ala
         -5              -1
```

EXAMPLE 5

Amino Acid Distribution

The amino acid distribution of the mature pullulanase, determined from the amino acid sequence of pullulanase (Example 4), is summarized in Table 2.

TABLE 2

| Symbol | Amino acids | Number | (by molecular weight) % |
|---|---|---|---|
| D | aspartic acid | 75 | 8.5 |
| N | asparagine | 69 | 7.7 |
| V | valine | 72 | 7.0 |
| T | threonine | 70 | 6.9 |
| Y | tyrosine | 42 | 6.7 |
| L | leucine | 60 | 6.7 |
| K | lysine | 48 | 6.0 |
| S | serine | 64 | 5.5 |
| I | isoleucine | 47 | 5.2 |
| E | glutamic acid | 40 | 5.1 |
| Q | glutamine | 39 | 4.9 |
| A | alanine | 69 | 4.8 |
| P | proline | 46 | 4.4 |
| G | glycine | 75 | 4.2 |
| F | phenylalanine | 27 | 3.9 |
| W | tryptophan | 18 | 3.3 |
| M | methionine | 23 | 3.0 |
| H | histidine | 22 | 3.0 |
| R | arginine | 18 | 2.8 |
| X | unknown | 3 | 0.3 |
| C | cysteine | 1 | 0.1 |

EXAMPLE 6

Determination of the Isoelectric Point

IEF (isoelectrofocusing) electrophoresis is carried out on solution C, as obtained in Example 2, in a pH gradient varying from 4.0 to 6.5.

A volume corresponding to 0.12 pullulanase units is deposited in triplicate on the gel. After migration, one third of the gel is coloured with Coomassie blue.

The other two portions of the gel are covered by agar gels (1% weight/volume) buffered with 100 mM CH₃COONa, 1 mM CaCl₂ and 1 mM MgCl₂ (pH 4.5) and containing, respectively, 0.1% (w/v) of AZCL-pullulane or 1% (w/v) of amylopectin. The combination (acrylamide gel/agar gel) thus obtained is then incubated at 60° C. in an atmosphere of saturated humidity for 16 hours. The gel covered by the top layer of amylopectin is then incubated at room temperature in a solution containing 3 mM I₂ and 50 mM KI in order to demonstrate the debranching activity by appearance of the blue coloration.

Development of the iodine of the amylopectin gel reveals a deep blue halo, indicating a debranching activity, at an isoelectric point between about 4.1 and about 4.5 for the enzyme of the present invention. Development of the pullulanase activity indicates the same result.

This demonstrates that the pullulanase of the present invention has a pullulanase activity and a debranching activity.

This demonstrates that the pullulanase of the present invention is capable of hydrolysing bonds of the α-1,6 type, both in pullulane and in amylopectin. This demonstrates a low specificity of the pullulanase of the present invention with respect to its substrate.

This is confirmed by the estimation made starting from the amino acid sequence of the mature form of the pullulanase (without the signal sequence) as described in Example 4, and an isoelectric point of 4.5 is deduced by calculation.

EXAMPLE 7

Activity Profile as a Function of pH and Temperature for the Pullulanase Produced by the Natural Strain (*Bacillus deramificans*)

The enzymatic activity of the pullulanase is measured at various temperatures (55°, 60° and 65° C.) and at various pH values (from 3.25 to 7) in 50 mM citrate/phosphate buffer by measuring the reducing sugars released. Solution C of pullulanase as obtained in Example 2, diluted to about 1 PUN/ml, is used.

The results are summarized in Table 3.

In the course of this test, the maximum enzymatic activity was measured by measuring the reducing sugars released for a sample placed at a pH of about 4.3 and at a temperature of about 60° C. over a period of 15 minutes. By definition, a relative enzymatic activity of 100% was thus attributed to this sample.

This example shows that the pullulanase according to the invention has an optimum enzymatic activity, measured at a temperature of about 60° C., in a pH range of between 4.0 and 4.8.

This example also shows that the pullulanase according to the invention has an optimum enzymatic activity, measured at a pH of about 4.3, in a temperature range of between 55° and 65° C.

Furthermore, this example shows that the pullulanase according to the invention develops an enzymatic activity of more than 80% of the maximum enzymatic activity in a pH range of between about 3.8 and about 4.9.

TABLE 3

| | Relative activity of the enzyme % | | |
|---|---|---|---|
| | Temperature °C. | | |
| pH | 55 | 60 | 65 |
| 3.25 | 5.7 | 2.2 | 4.3 |
| 3.75 | 80.8 | 83.7 | 11.5 |
| 4.30 | 87.9 | 100 | 84.1 |
| 4.90 | 82.4 | 87.1 | 68 |
| 5.50 | 50.6 | 39.6 | 13.5 |
| 6.00 | 7.5 | 2.9 | 0 |
| 6.40 | 0 | 0 | 0 |

EXAMPLE 8 pH Stability of the Pullulanase Produced by the Natural Strain (*Bacillus deramificans*)

Solution A of the pullulanase as obtained in Example 2 is diluted such that it develops an enzymatic activity of about 0.7 PUN/ml in various 100 mM citrate/phosphate buffers at pH values varying between pH 3.0 and 7.0. The various dilute solutions containing the pullulanase are incubated at 60° C. for 60 minutes.

The enzymatic activity of these different solutions after incubation for 60 minutes at pH 4.2 at 60° C. in the presence of 1.6% (weight/volume) of pullulane is then measured. The amount of maltotriose formed is measured by HPLC chromatography (as described in Example 2). The results are summarized in Table 4.

In the course of this test, the maximum enzymatic activity was measured for a sample placed at a pH of about 4.5 and at a temperature of about 60° C. By definition, a relative enzymatic activity of 100% was thus attributed to this sample.

This example shows that the pullulanase according to the invention is stable in a wide acid pH range, and in fact it has a relative enzymatic activity of at least 85%, measured after incubation for 60 minutes at a temperature of about 60° C. in the absence of substrate and in a pH range of between about 3.5 and about 5.8. This example also shows that it has a relative enzymatic activity greater than 90%, measured in a pH range of between about 3.8 and about 5 under these same conditions, and that it is inactivated only at a pH of less than or equal to 3 or greater than or equal to 7.

TABLE 4

| pH | Relative activity % |
|---|---|
| 3 | 0 |
| 3.5 | 90 |
| 4 | 98 |
| 4.5 | 100 |
| 5 | 96 |
| 5.5 | 92 |
| 6 | 89 |
| 6.5 | 75 |
| 7 | 0 |

EXAMPLE 9

Determination of the Half-life of the Pullulanase Produced by the Natural Strain (*Bacillus deramificans*)

Solution C of the pullulanase as obtained in Example 2 is diluted such that it develops an enzymatic activity of about 0.7 PUN/ml in a 100 mM sodium acetate buffer at a pH of 4.5. The dilute solution containing the pullulanase is incubated at 60° C. and samples are taken at various times.

The enzymatic activity is then measured by the reducing sugars method (method of SOMOGYI described above).

In the course of this test, the maximum enzymatic activity was measured for the sample at time 0. By definition, a relative enzymatic activity of 100% was thus attributed to this sample.

The results are summarized in Table 5.

TABLE 5

| Time hours | Relative activity % |
|---|---|
| 0 | 100 |
| 16 | 76 |
| 24 | 74 |
| 40 | 57 |
| 48 | 54 |
| 64 | 47 |

This example shows that the pullulanase is heat stable at an acid pH.

This example shows that the half-life of the pullulanase is about 55 hours under these conditions. In fact, the pullulanase has a relative enzymatic activity of at least 50%, measured after an incubation of 55 hours at a temperature of about 60° C. in a solution buffered at a pH of about 4.5 and in the absence of substrate.

This example shows moreover that the pullulanase according to the invention has a relative enzymatic activity of at least 55%, measured after an incubation of 40 hours at a temperature of about 60° C. in a solution buffered at a pH of about 4.5 and in the absence of substrate. This example also shows that it has a relative enzymatic activity of at least 70%, measured after an incubation of 24 hours under these same conditions.

EXAMPLE 10 AND EXAMPLE 11R (COMPARISON)

Saccharification

A saccharification medium is prepared by suspending, in water, maize starch at a concentration of 35% (weight/weight) by weight of starch dry matter and calcium chloride at a concentration of 0.02% (weight/volume).

This maize-starch suspension is liquefied in the presence of α-amylase, sold under the trade name TAKATHERM® L-340 by SOLVAY ENZYMES, at 105° C. for 5 minutes at pH 6.0.

The liquefied starch thus obtained is cooled rapidly to a temperature of 95° C. and the hydrolysis is continued for 120 minutes at 95° C., while stirring. At this stage, the degree of hydrolysis is between 10 and 12 DE (DE represents the unit of "dextrose equivalents", that is to say the number of reducing ends expressed as glucose equivalent).

The liquefied starch thus obtained is diluted to a final concentration of 32 g of dry weight per 100 g of saccharification medium.

The saccharification medium obtained is cooled to a temperature of 60° C.

The pH of this saccharification medium is adjusted to various values of from 3.9 to 4.8 with acetic acid and is kept constant in the course of the saccharification.

An amount of glucoamylase corresponding to 0.176 DU/g.ds (enzymatic units of glucoamylase per g of dry matter of the saccharification medium) is added to the saccharification medium the glucoamylase used being sold under the trade name DIAZYME L-200 by SOLVAY ENZYMES.

For Example 10 according to the invention, an amount of pullulanase corresponding to 0.075 PUN/g of dry matter is also added to the saccharification medium in the form of an aqueous concentrated solution of pullulanase (solution A) as described in Example 2.

Comparison Example 11R is carried out as described above for Example 10, but without addition of pullulanase.

After 48 hours, the saccharification is stopped and the products obtained are analysed by chromatography (as described in Example 2).

The results are summarized in Table 6.

This example shows that the pullulanase according to the invention is effective in saccharification. The pullulanase of the invention thus has all the appropriate properties compatible with the actual industrial conditions of saccharification of starch.

This example shows that the starch conversion level is greater in the presence of the pullulanase according to the invention at various pH values down to a highly acid pH, that is to say to at least 3.9.

TABLE 6

| pH | Examples | Products obtained in % | | | |
|---|---|---|---|---|---|
| | | Glucose | DP2 | DP3 | >DP3 |
| 3.9 | 11R | 94.18 | 2.92 | 0.54 | 2.37 |
| | 10 | 95.63 | 2.90 | 0.73 | 0.73 |
| 4.2 | 11R | 94.18 | 2.98 | 0.56 | 2.29 |
| | 10 | 94.79 | 4.30 | 0.56 | 0.38 |
| 4.5 | 11R | 93.72 | 2.88 | 0.57 | 2.83 |
| | 10 | 95.49 | 3.00 | 0.75 | 0.76 |
| 4.8 | 11R | 93.32 | 2.79 | 0.60 | 3.30 |
| | 10 | 95.25 | 2.70 | 0.87 | 1.18 |

DP2 represents the oligosaccharides containing two glucose units (glucose dimer), DP3 the oligosaccharides containing three glucose units (glucose trimer) and >DP3 the oligosaccharides containing more than 3 glucose units.

EXAMPLE 12 AND EXAMPLE 13R (COMPARISON)

Saccharification

Example 10 is repeated, but the pH of the saccharification medium is fixed at a pH of 4.2.

An amount of glucoamylase corresponding to 0.17 DU/g.ds (enzymatic units per g of dry matter of the saccharification medium) is added to the saccharification medium, the glucoamylase used being sold under the trade name DIAZYME L-200 by SOLVAY ENZYMES.

For Example 12 according to the invention, various amounts of pullulanase corresponding to, respectively, 0.0325 PUN/g.ds., 0.050 PUN/g.ds., 0.075 PUN/g.ds. and 0.10 PUN/g.ds. (enzymatic units of pullulanase per gram of dry matter of the saccharification medium) are also added to the saccharification medium in the form of an aqueous concentrated solution of pullulanase (solution A) as described in Example 2.

Comparison Example 13R is carried out as described above for Example 12, but without addition of pullulanase.

The results are summarized in Table 7.

This example shows that the amount of pullulanase which it is necessary to use to observe an increase in the percentage of glucose produced less than 0.0325 PUN/g.ds.

TABLE 7

| Examples | Pullulanase PUN/g.ds. | Products obtained in % | | | |
|---|---|---|---|---|---|
| | | Glucose | DP2 | DP3 | >DP3 |
| 13R | 0 | 94.78 | 3.55 | 0.73 | 0.94 |
| 12 | 0.0325 | 95.16 | 3.45 | 0.78 | 0.61 |
| | 0.050 | 95.30 | 3.39 | 0.74 | 0.56 |
| | 0.075 | 95.25 | 3.47 | 0.74 | 0.55 |
| | 0.10 | 95.27 | 3.49 | 0.70 | 0.53 |

EXAMPLE 14

Construction of the Plasmid pUBDEBRA1

The plasmid pUBDEBRA1 (FIG. 1) contains the gene which codes for the pullulanase of the strain *Bacillus deramificans* T 89.117D under the control of its own transcription promoter introduced into the vector pUB131. Construction of the plasmid pUBDEBRA1 is described below.

The chromosomal DNA is extracted and purified from a culture of the strain *Bacillus deramificans* T 89.117D (identified under the number LMG P-13056).

For this purpose, a culture of 200 ml of this bacillus is carried out in liquid MYE medium (Example 1).

When this culture has been realized and is in the stationary phase, it is centrifuged (BECKMAN JA-10 rotor) at 5000 revolutions per minute for 10 minutes. The centrifugation pellet thus obtained is taken up in 9 ml of buffer comprising 0.1M TRIS-HCl (tris(hydroxymethyl)-aminomethane acidified with HCl) at a pH of 8, 0.1M EDTA (ethylenediaminetetraacetic acid) and 0.15M NaCl containing 18 mg of lysozyme, and the suspension thus obtained is incubated for 15 minutes at 37° C.

The lysate thus obtained is then treated with 200 μl of a solution of 10 mg/ml of RNAse at 50° C. for 20 minutes. 1 ml of a 10% strength solution of SDS (sodium dodecyl sulphate) is then added to this lysate. This lysate is then incubated for 30 minutes at 70° C.

The lysate is then cooled to about 45° C. and 0.5 ml of a solution of 20 mg/ml of proteinase K (prepared extemporaneously) is then added thereto.

The lysate is incubated at 45° C., while stirring manually, until a transparent solution is obtained.

Several extractions with phenol are carried out on this transparent solution under the conditions and in accordance with the procedures described in Molecular Cloning—a laboratory manual—SAMBROOK, FRITSCH, MANIATIS—second edition, 1989, on page E.3, until a proper interface, as described there, is obtained.

The DNA is precipitated by 20 ml of ethanol. The precipitate is collected by centrifugation at 5000 revolutions per minute for 5 minutes, and is then suspended in 2 ml of TE buffer at pH 8.0 (10 mM TRIS-HCl, 1 mM EDTA at pH 8.0).

The DNA thus obtained is then partly cleaved by the restriction enzyme Sau3AI. The restriction conditions in this example and in all the other examples of this application are those described by SAMBROOK et al. (page 5.28–5.32), except that these restriction conditions are increased by a factor of 10 in order to obtain a sufficient amount of DNA for the following purification stages.

The ratio between the amount of DNA used and the amount of enzyme is adjusted in order to obtain a maximum of fragments of a size between 5 and 10 kbp (kbp: $10^3$ base pairs).

The combined fragments thus obtained are then subjected to agarose gel electrophoresis (0.8%) as described by SAMBROOK et al. (page 6.01–6.19), and the fragments of a size between 5 and 10 kbp are isolated and purified by the GENE CLEAN method. They are then spliced with the plasmid pBR322, which is sold by the company BIOLABS [CLONTECH LABORATORIES (USA) catalogue No. 6210-1], cut at the BamHI site and dephosphorylated as described by SAMBROOK et al. (page 1.60–1.61). This same technique is used in the other examples.

The splice thus obtained is transformed into cells of *E. coli* MC1061 [CLONTECH LABORATORIES, catalogue No. C-1070-1] by electroporation (SAMBROOK et al., page 1.75–1.81); the transformed strains are selected on a Petri dish containing LB (Luria-Bertani) agar-agar medium and 100 μg/ml of ampicillin, after growth at 37° C. for about 18 hours. The LB medium is described by SAMBROOK et al. (page A.4). This medium contains 10 g/l of tryprone, 5 g/l of yeast extract and 10 g/l of sodium chloride.

The colonies obtained on these dishes are then replicated on two dishes of the same medium.

One of the two dishes is covered with an agar-agar medium containing 1% (w/v) of agar, 100 mM sodium acetate (pH 4.5) and 0.1% (w/v) of AZCL-pullulane. After incubation at 60° C. for 18 hours, the colony showing the largest zone of hydrolysis of the AZCL-pullulane is identified and the corresponding colony is isolated on the other replicated dish.

A strain is thus obtained from which the plasmid called pBRDEBRA3 is extracted. The EcoRi-BamHI fragment of about 4.6 kbp of the plasmid pBRDEBRA3 is obtained by double digestion of the plasmid pBRDEBA3 with BamHI and EcoRI, and purification by agarose gel electrophoresis (0.8% w/v). This fragment is then spliced with the vector pUB131 (described in European Patent Application 0 415 296), which was previously the subject of double digestion with BamHI and EcoRI at the BamHI and EcoRI sites using the strain *Bacillus subtilis* PSL1 as the host.

The strain *Bacillus subtilis* PSL1 can be obtained from the B.G.S.C. collection under number 1A510 (BACILLUS GENETIC STOCK CENTER, Ohio State University, United States).

The plasmid pUBDEBRA1 thus obtained is isolated and purified from transformed PSL1 cells by the technique of alkaline lysis (SAMBROOK et al., page 1.25–1.28). This same technique is used in the other examples.

All the transformed strains of *Bacillus subtilis* are capable of expressing the gene of pullulanase and of secreting pullulanase.

The transformed PSL1 strains containing the plasmid pUBDEBRA1 are subcultured on a Petri dish containing LB medium with 25 μg/ml of kanamycin.

The colonies obtained are covered by a top layer of agarose (1% weight/volume) containing AZCL-pullulane (0.1% weight/volume) and sodium acetate (100 mM, pH 4.5). After incubation at 60° C. for 18 hours, it is found that all the colonies of the transformed strains are surrounded by a hydrolysis halo of AZCL-pullulane.

EXAMPLE 15

Preparation of the Strain *Bacillus licheniformis* SE2 delap1

Identification of the terminal parts of the gene of the alkaline protease of the host strain of *Bacillus licheniformis* SE2

This example relates to identification of the terminal parts of the gene of the alkaline protease of the host strain of *Bacillus licheniformis* in order to prepare the deletion plasmid for deletion of the said gene of *Bacillus licheniformis* SE2.

1. Extraction of the chromosomal DNA from *B. licheniformis* SE2

In order to isolate the gene of the alkaline protease of the chromosomal DNA of *Bacillus licheniformis* SE2, the chromosomal DNA is first extracted in accordance with the method described in Example 14 for extraction of chromosomal DNA, except that the culture medium comprises LB medium and is purified.

2. Identification of the C-terminal part of the gene of the alkaline protease

The chromosomal DNA extracted is subjected to a restriction analysis described in Molecular Cloning—SAMBROOK et al. (page 1.85) and Molecular Cloning, a laboratory Manual, MANIATIS et al., 1982 Cold Spring Harbor Laboratory, pages 374–379. The DNA fragments obtained from these digestions are separated according to their size on an 0.8% (weight/volume) agarose gel.

The agarose gel is then subjected to analysis by the SOUTHERN BLOT technique (technique described by SAMBROOK et al.—page 9.31) in order to identify the fragments which contain the nucleotide sequences of the C-terminal part of the gene of the alkaline protease.

The probe constructed, which is used for the hybridizations, is a synthetic oligonucleotide corresponding to the C-terminal part of the gene of the alkaline protease. The technique used to construct the synthetic oligonucleotide is described in BEAUCAGE, S.L. et al. (1981), Tetrahedron Letters, 22, pages 1859–1882, using β-cyanoethyl-phosphoramidites in a BIOSEARCH CYCLONE SYNTHESIZER apparatus. The synthetic oligonucleotide sequence which was constructed is as follows (SEQ ID NO:2)

5'-GGCGGAGCAAGCTTTGTGG-3'

These results show that the C-terminal part of the gene of the alkaline protease is located on the PstI fragment of about 2.7 kbp.

The hybridization with the DNA probes is carried out in accordance with the technique described in Molecular Cloning—SAMBROOK et al.—page 9.52–9.55. This same technique is used in the other examples.

The preparation of the extracted chromosomal DNA originating from the strain of *Bacillus licheniformis* SE2 is then digested with the enzyme PstI and the fragments obtained are separated according to their size by agarose gel electrophoresis (0.8%).

The PstI fragments obtained of about 2.7 kbp are extracted from the gels and purified by the so-called "GENE CLEAN" technique, which uses glass beads and is marketed by the company BIO101 (USA).

The PstI fragments of 2.7 kbp are then spliced (SAMBROOK et al., page 1.68–1.69) with the plasmid pUC18 (CLONTECH Laboratories, No. 6110-1) which has first been digested at the PstI site and dephosphorylated. The splice thus obtained was then transformed into the cells of *Escherichia coli* MC1061 by the technique with CaCl$_2$ (SAMBROOK et al.—page 1.82–1.84). The technique which allows dephosphorylation of the DNA fragments or linearization of the vectors is described by SAMBROOK et al. (page 1.60–1.61). The splicing technique is also described by SAMBROOK et al. (page 1.68–1.69).

The transformed strains are selected on Petri dishes containing LB agar-agar medium supplemented with 100 µg/ml of ampicillin. The strains transformed starting from *E. coli* MC1061 thus obtained are then selected by hybridization with the synthetic oligonucleotide labelled using the C-terminal probe used in the SOUTHERN study and the plasmid pKC1 is isolated.

The synthetic oligonucleotide is labelled by phosphorylation with $^{32}P$-γ-ATP using the T4 polynucleotide kinase of the phage T4 and in accordance with the technique described by SAMBROOK et al. (page 11.31–11.33).

3. Identification of the N-terminal part of the gene of the alkaline protease

The chromosomal DNA extracted is subjected to restriction analysis. The DNA fragments obtained from these digestions are separated according to their size on a 0.8% agarose gel.

The agarose gel is then subjected to analysis by the SOUTHERN BLOT technique in order to identify the fragments which contain the nucleotide sequences of the N-terminal part of the gene of the alkaline protease.

The probe which is used for the hybridizations is a synthetic oligonucleotide corresponding to the N-terminal part of the gene of the alkaline protease. The sequence of the synthetic oligonucleotide which has been constructed is as follows (SEQ ID NO:3):

5'-ATGGCTCCTGGCGCAGGC-3'

These results show that the N-terminal part of the gene of the alkaline protease is located on the PstI fragment of about 5.5 kbp and also on a smaller BclI-PstI fragment of about 2 kbp. This fragment does not contain the restriction sites XbaI, ClaI, HpaI and SphI.

The preparation of the extracted chromosomal DNA originating from the strain of Bacillus licheniformis SE2 is then digested with the enzyme PstI and the fragments obtained are separated according to their size by agarose gel electrophoresis (0.8%).

The fragments obtained of about 5.5 kbp are extracted from the gels and purified by the so-called "GENE CLEAN" technique (company BIO 101).

The PstI fragments of 5.5 kbp thus obtained are then subjected to a series of digestions with BclI, XbaI, ClaI, HpaI and SphI. The DNA fragments thus produced are spliced with the plasmid pMK4 (as described in SULLIVAN et al., (1984), Gene 29, pages 1–26) which has first been linearized by BamHI and PstI. The plasmid pMK4 can be obtained from the B.G.S.C. collection (Bacillus Genetic Stock Center (Ohio State University) Columbus, Ohio, USA) under number 1E29.

The splices thus obtained were then transformed into the cells of *Escherichia coli* MC1061 by the technique with CaCl$_2$.

The transformed strains are selected on Petri dishes containing LB agar-agar medium supplemented with 100 µg/ml of ampicillin. The strains transformed starting from *E. coli* MC1061 thus obtained are then selected by hybridization with the synthetic oligonucleotide labelled using the N-terminal probe in the SOUTHERN study and the plasmid pKP1 is isolated.

EXAMPLE 16

Sequences of the Alkaline Protease

The sequences of the fragments introduced into the plasmids pKP1 and pKC1 are determined from the Pst1 sites up to the SacI sites in accordance with the technique described by SAMBROOK et al. (pages 13.15 and 13.17 and FIG. 13.3B).

EXAMPLE 17

Construction of the Plasmid pLD1

The plasmid pLD1 (FIG. 2) is constructed with the aim of preparing the strain *Bacillus licheniformis* SE2 delap1. The construction of the plasmid pLD1 is described below.

The plasmid pKP1 (as obtained in Example 15) is unstable in *E. coli* MC1061. For this reason, the chromosomal DNA fragment containing the N-terminal part of the gene of the alkaline protease of *B. licheniformis* SE2 was introduced into the vector pACYC184 (BIOLABS, USA, under number #401-M). This introduction was carried out by introducing the EcoRI-EcoRI fragment of 1849 bp of the plasmid pKP1 into the EcoRI site of the plasmid pACYC184 and the splicing is used to transform the cells of *E. coli* MC1061. The plasmid pKPN11 is thus obtained.

The transformed strains are selected on a Petri dish containing LB agar-agar medium supplemented with 12.5 μg/ml of tetracycline. The orientation of the EcoRI-EcoRI fragment of 1849 bp in the plasmid pKPN11 is determined by restriction analysis (SAMBROOK et al.—page 1.85 and MANIATIS et al.—page 374–379).

The plasmid pKPN12 is obtained in the following manner: the StyI-StyI fragment of 1671 bp of the plasmid pKPN11 is removed by digestion with StyI, followed by replacement of this fragment by the following synthetic double-stranded DNA, which has been produced beforehand:

```
5'-CTTG GAGCTC GTTAAC AGATCT        -3' (SEQ ID NO:4)
3'-     CTCGAG CAATTG TCTAGA GTTC-5' (SEQ ID NO:5)
    (StyI) SacI  HpaI    BalII  (StyI)
```

Digestion of plasmids with restriction enzymes is carried out in accordance with the technique described by SAMBROOK et al.—1989—chapters 5.28–5.32.

The DNA fragment originating from the plasmid pUB131 which codes for the resistance to kanamycin and to bleomycin or to phleomycin was obtained as follows:

The PstI-TaqI fragment of 2666 bp, which carries the genes which code for resistance to kanamycin and to bleomycin or to phleomycin, is obtained by double digestion of PstI-TaqI of the plasmid pUB131. This fragment is introduced into the PstI-AccI sites of the plasmid pBS- (STRATAGENE, USA, under number 211202). The plasmid pBSKMPM is thus obtained.

During the preparation of the plasmid pBSKMPM, a small deletion in the region of the bond with the plasmid pBS- appears, which causes the loss of the SphI and PstI sites in the plasmid pBSKMPM. The plasmid pBSKMPM is used to produce a single-stranded DNA used to effect site-directed mutagenesis with the aim of introducing the two synthetic nucleotides, the SmaI sites of which are identified below, one being situated in front of and the other after the genes of resistance to kanamycin and to phleomycin.

The technique of site-directed mutagenesis is described by SAMBROOK et al.—page 15.74–15.79. It uses the mutagenesis kit sold by BIO-RAD (No. 170-3576).

The sequences of the synthetic oligonucleotides used for the mutagenesis are as follows (SEQ ID NO:6 and SEQ ID NO:7 respectively):

```
5'-CAT CTAATCTTCAACACCCGGGCCCGTTTGTTGAAC-3'
                       SmaI
```

```
5'-CAAAATAAAAAAGATACAACCCGGGTCTCTCGTATCTTTTAT-3'
                            SmaI
```

The plasmid obtained by this mutagenesis in the presence of the two oligonucleotides is the plasmid pBSKMPM1. This plasmid contains two SmaI restriction sites which allow isolation of the DNA fragment containing the genes which code for resistance to kanamycin and phleomycin.

The SmaI-SmaI fragment of 1597 bp of the plasmid pBSKMPM1 is then introduced into the SmaI site of the plasmid pKPN12, and the plasmid pKPN14 is thus obtained.

Proper orientation of the fragment introduced into the plasmid pKPN14 is verified by carrying out a selection on preparations of plasmid DNA by restriction analysis (SAMBROOK et al.—page 1.85).

The DNA fragment present on the plasmid pKC1 and located before the N-terminal sequence of the alkaline protease is isolated on the SacI-HindIII fragment of 1.2 kbp of the plasmid pKC1 (as obtained in Example 15) by digestion, initially with HindIII.

The projecting 5' end of HindIII is rendered blunt-ended by treatment with the Klenow fragment of DNA polymerase (SAMBROOK et al.—page F.2–F.3). The SacI restriction is thus effected in order to produce the desired blunt-ended SacI-HindIII fragment. This fragment is introduced into the HpaI and SacI sites of the plasmid pKPN14, producing the plasmid pLID1.

All these constructions are effected by transformation of the strain *E. coli* MC1061 in the presence of tetracycline (12 μ/ml) for selection of the transformed strains.

A plasmid which is capable of multiplying in *B. subtilis* and in *B. licheniformis* is constructed from the plasmid pLID1 by replacing the replication functions of the *E. coli*, which are carried by the BglII-BglII fragment of 3623 bp of the plasmid pLID1, by the fragment which carries the replication functions of the Bacillus: fragment BglII-BamHI of 2238 bp isolated from the plasmid pUB131.

Figure 2:
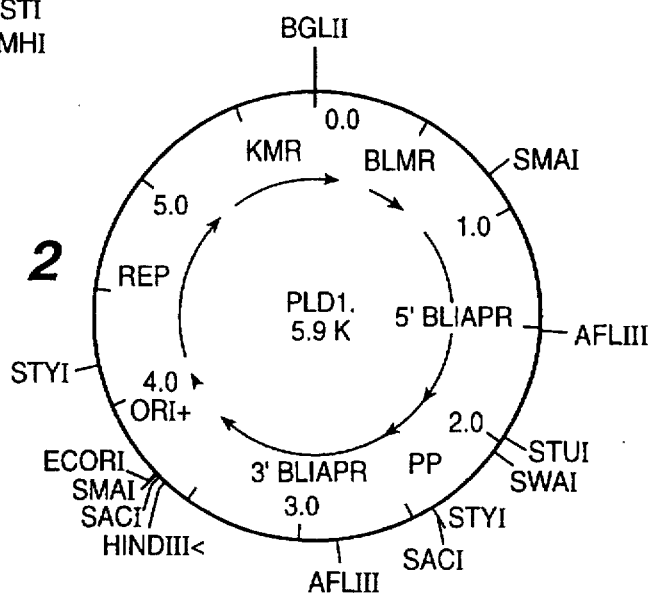
FIG. 2 shows the restriction map of the plasmid pLD1.

This replacement of replication functions of *E. coli* by Bacillus cells was effected by first isolating the BglII-BglII fragment of 3.6 kbp from the plasmid pLID1 by digestion of the plasmid pLID1 with BglII and BamHI. Supplementary BamHI digestion was necessary, and in fact BglII digestion alone would result in fragments of identical size which could not be separated by agarose gel electrophoresis. The BglII-BglII fragment of 3.6 kbp is thus cloned in the strain of *Bacillus subtilis* SE3 in the fragment BglII-BamHI of 2238 bp which has been isolated from the plasmid pUB131, producing the plasmid pLD1 (FIG. 2).

The strain *Bacillus subtilis* SE3 was deposited on 21 Jun. 1993 at the collection called the BELGIAN COORDINATED COLLECTIONS OF MICROORGANISMS in accordance with the Treaty of Budapest under number LMG P-14035.

EXAMPLE 18

Construction of *Bacillus licheniformis* SE2 Delap1

The desired modifications in the chromosomal DNA of the strain Bacillus licheniformis SE2 are effected by techniques based on homologous recombination. The modifications are effected to produce the strain *Bacillus licheniformis* SE2 delap1.

The plasmid pLD1 is transformed in *B. licheniformis* SE2 by the protoplast technique described by Molecular Biological Methods for Bacillus (pages 150–151) and under the conditions defined, except for the following modifications: the lysozyme powder is added in an amount of 5 mg/ml in the SMMP, instead of 1 mg/ml as defined in stage 7 of the procedure described, the incubation period to obtain maximum lysis with the lysozyme is 60 minutes, and the regeneration is carried out in DM3 medium (described by Molecular Biological Methods for Bacillus (HARWOOD et al., eds) John Wiley and Sons (1990) (pages 150–151)) containing 200 µg/ml of kanamycin.

A transformed strain is isolated and the restriction map of the plasmid pLD1 introduced into this strain is verified.

The transformed strain is cultured in 50 ml of an LB medium supplemented with 2 g/l of glucose and 25 µg/ml of kanamycin for 18 hours at 37° C.

A sample of culture (0.1 ml) is taken and used to inoculate a conical flask containing 50 ml of the same LB medium. The culture is incubated at 37° C. for 18 hours. A sample of this culture is taken and tested on a Petri dish containing LB agar-agar medium supplemented with 25 µg/ml of kanamycin and 1% (weight/volume) of skimmed milk (DIFCO) to detect the presence of protease.

The absence of a hydrolysis halo around the colonies which show growth on these Petri dishes indicates that these colonies are unable to produce an alkaline protease.

The cultures and tests are repeated until a strain (apr$^-$, Km$^r$), that is to say both no longer producing alkaline protease (apr$^-$) and resistant to kanamycin (Km$^r$), is obtained.

The plasmid pLD1 present in this strain of *Bacillus licheniformis* SE2 delap1 is then removed from it by culture on a growth medium at 37° C. in the absence of antibiotic.

This strain is cultured in 50 ml of LB medium supplemented with 2 g/l of glucose for 18 hours at 37° C. A volume of 0.1 ml of this culture is taken and used to inoculate another conical flask also containing 50 ml of the same medium, culture lasting 18 hours at 37° C. A sample is then taken and is spread out on a Petri dish containing LB medium. The colonies isolated are subcultured on a second dish of LB medium supplemented with 25 µg/ml of kanamycin. A strain which is sensitive to kanamycin (Km$^s$) is isolated. Its phenotype is confirmed (apr$^-$, Km$^s$).

The chromosomal DNA of this strain is then isolated and purified and the structure of the chromosomal deletion is verified by the SOUTHERN BLOT technique. The deletions identified are correct as regards their position, having taken place by homologous double recombination in the sequences situated before (5') and after (3') in the gene of the alkaline protease.

The strain obtained is called *B. licheniformis* SE2 delap1. It does not produce alkaline protease.

EXAMPLE 19

Transformation of *Bacillus licheniformis* SE2 Delap1 with the Expression Vector The plasmid pUBDEBRA1 (FIG. 1) described in Example 14 is extracted from its host, isolated and purified (SAMBROOK et al., 1989, pages 1.25–1.28).

A culture of the strain *B. licheniformis* SE2 delap1 described in Example 18 is prepared and this strain is then transformed with this plasmid in accordance with the protoplast technique described by MANIATIS et al. (pages 150–151).

The transformed strain is selected on a Petri dish, isolated and purified by screening.

EXAMPLE 20

Production of Pullulanase by *B. licheniformis* SE2 Delap1 (pUBDEBRA1)

The strain *B. licheniformis* SE2 delap1 transformed by the plasmid pUBDEBRA1 as obtained in Example 19 is cultured for 17 hours at 37° C. in a preculture LB medium supplemented with 0.5% (w/v) of glucose and 20 µg/ml of kanamycin. This preculture is transferred (5% v/v) into 50 ml of M2 medium supplemented with 20 µg/ml of kanamycin. The M2 medium contains 30 g of soya flour, 75 g of soluble starch, 2 g of sodium sulphate, 5 mg of magnesium chloride, 3 g of NaH$_2$PO$_4$, 0.2 g of CaCl$_2$.H$_2$O and 1000 ml of water. The pH of this M2 medium is adjusted to 5.8 with 10N NaOH before its sterilization. The culture is incubated, while stirring, for 80 hours at 37° C. After 80 hours, the biomass is eliminated by centrifugation at 5000 revolutions per minute for 10 minutes. The supernatant from the centrifugation is kept. The enzymatic activity of this supernatant is measured and the presence of a pullulanase activity is recorded.

EXAMPLE 21

Construction of *Bacillus licheniformis* SE2 Delap1 (pUBCDEBRA11DNSI)—Chromosomal Integration This example relates to integration of the gene which codes for the pullulanase into the chromosome of the strain *Bacillus licheniformis* SE2 delap1.

For this purpose, the EcoRI-BamHI fragment of 4.6 kb of the plasmid pBRDEBRA3 is cloned into the EcoRI and BamHI sites of the pUBC131 vector by transformation of the strain *E. coli* MC1061, thus generating the plasmid pUBCDEBRA11.

Figure 3:
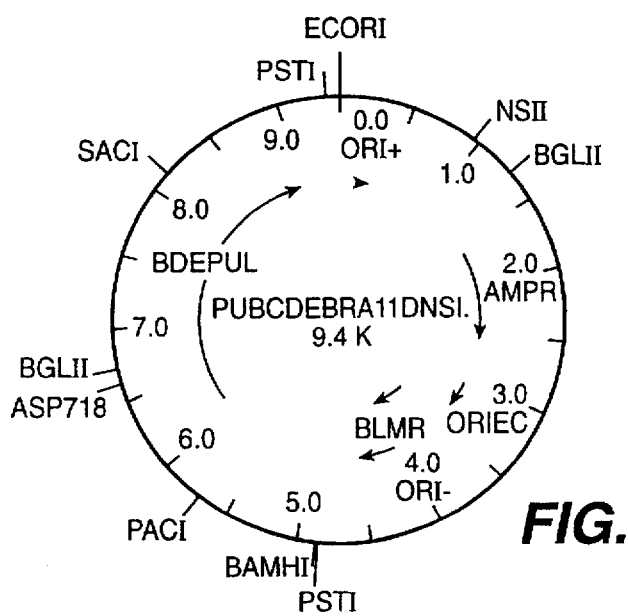
FIG. 3 shows the restriction map of the plasmid pUBCDEBRA11DNSI.

The integration vector pUBCDEBRA11DNSI (FIG. 3) is then constructed by deleting the NsiI-NsiI fragment of 886 bp of the plasmid pUBCDEBRA11. The plasmid thus obtained has lost the possibility of replicating itself in Bacillus owing to the loss of the NsiI fragment of 886 bp.

To effect this construction, the plasmid pUBCDEBRA11 is cleaved by the NsiI restriction enzyme and the NsiI-NsiI fragment of about 9.4 kbp is purified by agarose gel electrophoresis. This fragment is then subjected to splicing in order to recircularize it. The splicing is transformed into *E. coli* MC1061 and the plasmid pUBCDEBRA11DNSI1 is obtained.

In order to integrate the plasmid pUBCDEBRA11DNSI1 into the strain *B. licheniformis* SE2 delap1, it is necessary for this plasmid to carry a DNA fragment homologous to the chromosomal DNA. Chromosomal Sau3AI fragments originating from *B. licheniformis* were thus cloned into the BamHI site of the integration vector pUBCDEBRA11DNSI1.

For this purpose, the chromosomal DNA extracted from the strain *Bacillus licheniformis* SE2 delap1 is partially cleaved by the Sau3AI restriction enzyme. The DNA fragments of a size between 1.5 and 3 kb are then purified by agarose gel and spliced with the plasmid bUBCDEBRA11DNSI cleaved by the BamHI restriction enzyme and dephosphorylated. The splice thus obtained is transformed into the cells of MC1061 by electroporation. After selection on LB agar-agar medium containing 100 µg/ml of ampicillin, about 3000 colonies are obtained. All of these colonies are suspended in LB medium and the plasmids are extracted by the alkaline lysis technique (SAMBROOK et al., pages 1.25–1.28).

The preparation of plasmids thus obtained is thus introduced into the strain *Bacillus licheniformis* SE2 delap1 by transformation by the protoplast technique. The transformed cells are selected on DM3 regeneration medium (described in Molecular Biological Methods for Bacillus (Harwood, C. R. and Cutting, S. M., eds) J. Wiley and sons, 1990, pages 150–151) for their resistance to phleomycin (17 µg/ml), which can be conferred on them only by chromosomal integration of one of the plasmids constructed above.

The colonies thus obtained are subcultured on LB agar-agar medium supplemented with 5 µg/ml of phleomycin and 0.06% of AZCL-pullulane. The colony having the largest hydrolysis halo of AZCL-pullulane is then isolated and subcultured on LB agar-agar medium.

The plasmid content of this strain is then extracted. The preparation thus obtained is subjected to analysis by agarose gel electrophoresis, which shows the absence of plasmid.

The chromosomal DNA is extracted and purified as described in Example 14 and subjected to analysis by the SOUTHERN technique, which shows that the plasmid pUBCDEBRA11DNSI has been integrated into the chromosomal DNA by homologous recombination into an Sau3AI fragment of about 3 kb.

This demonstrates that the gene which codes for the pullulanase of *B. deramificans* is expressed in *B. licheniformis* in the integrated state in the chromosome.

EXAMPLE 22

Process for the Production of Pullulanase by the Strain *Bacillus licheniformis* SE2 delap1 (pUBCDEBRA11DNSI)

The strain *B. licheniformis* SE2 delap1 containing the gene of pullulanase in the integrated form in the chromosomal DNA as obtain in Example 21 is cultured for 17 hours at 37° C. in a preculture LB medium supplemented with 0.5% (w/w) of glucose and 5 µg/ml of phleomycin. A volume of 10 ml of this preculture is inoculated in 250 ml of M2 medium (described in Example 20) supplemented with 5 µg/ml of phleomycin in baffled flasks.

After incubation for 24 hours, while stirring, at 37° C., all of the culture thus obtained is introduced into a fermenter containing 6.5 l of M2 medium. Fermentation is continued for 72 hours at 37° C. The pH is kept at a value below 7.0 by addition of concentrated phosphoric acid, the air flow rate is kept at 4 litres/minute and the stirring is adjusted in order to obtain a dissolved oxygen content of greater than 30% (v/v) of the content of saturation.

After addition to the culture obtained of 50 ml of a flocculating agent based on polyamine, sold under the trade name OPTIFLOC® FC 205 by SOLVAY DEUTSCHLAND, the biomass is removed by centrifugation (BECKMAN JA-10) at 5000 revolutions/minute for 15 minutes and the supernatant obtained is acidified to pH 4.5 with a solution of 1M HCl. The solution obtained is centrifuged again at 8000 revolutions/minute for 15 minutes (BECKMAN JA-10).

The supernatant is then concentrated to a final volume of 1 liter by ultrafiltration using an ultrafiltration unit fitted with a membrane with a resolution limit of 5000 Daltons.

Acetone is then added to this concentrated solution to a final concentration of 60% (v/v). The suspension formed is incubated at 4° C. for 2 hours and then centrifuged at 8000 revolutions/minute for 15 minutes (BECKMAN JA-10). The centrifugation residue obtained is suspended in 100 ml of an aqueous solution containing 30% (w/v) of starch of the trade name MALTRIN® 250 (GRAIN PROCESSING CORPORATION), 0.3% (w/v) of sodium benzoate and 0.15% (w/v) of potassium sorbate at a pH of 4.5. The purified preparation of the pullulanase produced by the recombinant strain thus obtained is called solution D.

The activity of the pullulanase of solution D, measured by the reducing sugars method, is 150 PUN/ml.

EXAMPLE 23

Stability of the Pullulanase Produced by the Strain *Bacillus licheniformis* SE2 Delap1 (pUBCDEBRA11DNSI) with Respect to Temperature Solution D of pullulanase as obtained in Example 22 is diluted such that it develops an enzymatic activity of between 10 and 15 PUN/ml in a 0.05M citrate/phosphate buffer at a pH of 4.75.

This dilute solution containing the pullulanase is divided into 9 tubes in an amount of 5 ml of dilute solution per tube.

The various tubes containing the dilute solution are incubated in water baths at temperatures of between 40 and 80° C. for 75 minutes.

After this incubation, the tubes are placed in an ice bath for rapid cooling.

The enzymatic activity of the various solutions is then measured (measurement conditions: temperature of 60° C., pH of 4.5, incubation period of 15 minutes).

In the course of this test, the maximum enzymatic activity was measured for the sample placed at a pH of about 4.75 and at a temperature of about 55° C. By definition, a relative enzymatic activity of 100% was thus attributed to this sample.

The results are summarized in Table 12.

TABLE 12

| Temperature | Relative enzymatic activity % |
|---|---|
| 40 | 99 |
| 45 | 99 |
| 50 | 100 |
| 55 | 100 |
| 60 | 96 |
| 65 | 83 |
| 70 | 2 |
| 80 | 1 |

This example shows that the pullulanase according to the invention has a relative enzymatic activity of at least 80%, measured after an incubation of 75 minutes at a pH of 4.75 in the absence of substrate and in a temperature range of less than or equal to 65° C.

We claim:

1. A process for the production of isolated *Bacillus deramificans* pullulanase or a derivative or a mutant thereof, wherein said pullulanase or said derivative or said mutant catalyses hydrolysis of α-1,6-glucosidic bonds and comprises an N terminal sequence of Seq. ID No.: 1, comprising the steps of:

culturing the species *Bacillus deramificans* or a derivative or a mutant of *Bacillus deramificans* that retains all identifying characteristics of said species which produces said pullulanase in a suitable nutrient medium containing sources of carbon and nitrogen and mineral salts under aerobic conditions, and harvesting of the pullulanase obtained.

\* \* \* \* \*

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
       ( A ) LENGTH: 20 amino acids
       ( B ) TYPE: amino acid
       ( D ) TOPOLOGY: linear ( i i ) MOLECULE TYPE: peptide ( v ) FRAGMENT TYPE: N-terminal fragment ( v i ) ORIGINAL SOURCE:
       ( A ) ORGANISM: Bacillus deramificans
       ( B ) STRAIN: T 89.117D ( x i ) SEQUENCE DESCRIPTION: SEQ ID NO:1:

Asp Gly Asn Thr Thr Thr Ile Ile Val His Tyr Phe Cys Pro Ala Gly
 1               5                  10                  15

Asp Tyr Gln Pro
         20

( 2 ) INFORMATION FOR SEQ ID NO:2:

( i ) SEQUENCE CHARACTERISTICS:
       ( A ) LENGTH: 19 base pairs
       ( B ) TYPE: nucleic acid
       ( C ) STRANDEDNESS: single
       ( D ) TOPOLOGY: linear ( i i ) MOLECULE TYPE: nucleic acid (other);
       ( A ) DESCRIPTION: synthetic DNA ( x i ) SEQUENCE DESCRIPTION: SEQ ID NO:2:

GGCGGAGCAA GCTTTGTGG                                                                19

( 2 ) INFORMATION FOR SEQ ID NO:3:

( i ) SEQUENCE CHARACTERISTICS:
       ( A ) LENGTH: 18 base pairs
       ( B ) TYPE: nucleic acid
       ( C ) STRANDEDNESS: single
       ( D ) TOPOLOGY: linear ( i i ) MOLECULE TYPE: nucleic acid (other);
       ( A ) DESCRIPTION: synthetic DNA ( x i ) SEQUENCE DESCRIPTION: SEQ ID NO:3:

ATGGCTCCTG GCGCAGGC                                                                 18

( 2 ) INFORMATION FOR SEQ ID NO:4:

( i ) SEQUENCE CHARACTERISTICS:
       ( A ) LENGTH: 22 base pairs
       ( B ) TYPE: nucleic acid
       ( C ) STRANDEDNESS: single
       ( D ) TOPOLOGY: linear ( i i ) MOLECULE TYPE: nucleic acid (other);
       ( A ) DESCRIPTION: synthetic DNA ( x i ) SEQUENCE DESCRIPTION: SEQ ID NO:4:

CTTGGAGCTC GTTAACAGAT CT                                                            22

( 2 ) INFORMATION FOR SEQ ID NO:5:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: nucleic acid (other);
        ( A ) DESCRIPTION: synthetic DNA ( x i ) SEQUENCE DESCRIPTION: SEQ ID NO:5:

```
CTTGAGATCT GTTAACGAGC TC                                              22
```

( 2 ) INFORMATION FOR SEQ ID NO:6:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: nucleic acid (other);
        ( A ) DESCRIPTION: synthetic DNA ( x i ) SEQUENCE DESCRIPTION: SEQ ID NO:6:

```
CATCTAATCT TCAACACCCG GGCCCGTTTG TTGAAC                               36
```

( 2 ) INFORMATION FOR SEQ ID NO:7:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: nucleic acid (other);
        ( A ) DESCRIPTION: synthetic DNA ( x i ) SEQUENCE DESCRIPTION: SEQ ID NO:7:

```
CAAAATAAAA AAGATACAAC CCGGGTCTCT CGTATCTTTT AT                        42
```

( 2 ) INFORMATION FOR SEQ ID NO:8:

( i ) SEQUENCE CHARACTERISTICS:
        ( A ) LENGTH: 4464 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO:8:

```
GGATCCTGTT AGACTATTTG AGGAGTTTGC AACACTTGAT GTTTTATCCA AAGGAAGGGC      60
CGGAGATCAT CGCTGGTCGA GGTGCTTTCG GTGAAGCATT TTCGCTATTT TGGGTATAAC     120
CGGGCGCATT ACGATCAATT GTTTGAAGAG CATCTTGATT TACTTCAAAA GCTGAATGCT     180
TCGAAAAGAA TAACATGGAG CGGGCTTTAT CGAACACCTA TACATGATGC AGATATCGCA     240
CCCCGCCCTG TTCAGAAAAA CATTCCTTTG TGGGTTGGGG TGGGTGGGAC NMNTGAAASC     300
NS Y KCK Y Y GT GCRNVSNNNT ATGGTGC-
CGG CTTAGCATGG GTATTTGTC AGGCGATTGG        360
CTTCGGTTTA AGGCACTTTC GGACCTTTAT CGGCAGGCCG GCCAACAAGC ANGGTATTCA     420
CCGAACGATC TGAAAGTAGG AGTGACAGGG CATGCGTTTA TTGGAAAGAC GTCGCAGCAG     480
GCACTCAATG ACTATTACCC CTATCACGCG AATTATTGGC TAAACACTGAA CCAACAATTA    540
GGGCAGCCGT TACCCCAGCA ATACGTGAGG GAATTTAATT TATTAGCCTC CCCAGAGCAA    600
```

```
GCCTTATATG TGGGAAGCTC TCAACAAGTG GGCAGGNAAA AATTTTGCGC CAACATGAGG      660
NATTTGGTNA TAAACGTTTT ATCGCACAGA TCGACATTGG CGGAATGCCC TTTAAAACAG      720
TGGCCAAGAA TATTGAGCGG TTAGGCCACT GAGGTTGCAC CTGTCGTACG AAGAGCAACA      780
AGAGGGTAAT GGTAATAATC TATTTAACTG TTTATTAGAA AACTTGGTAT CTGTTTAATT      840
AAATAACAGG AGCCTGGAAG TGGGCCAAGG CTCCTTTCTA GGGAAACCTT TTTCTATTTA      900
TATAGGCGTT GTTGCCTAAG GCTAAGTAG GATTTTATTA AAAATATAGG AATTGCTCTT       960
TTATTCGACA CAATTATTCA ATGGAATACG ATAAAATGGA GAGTGTATGT AAGCGTTATA     1020
TTTTATTGGG GGGCTGATAG AAGAAAAGGG ATGCGACAGG GTCTATTAGC TAGTTTGGTA     1080
TTCGATTTCA GATCAATGCA ACGTACGAGT TTTTATTGA CTGCTTTGTG CAAGCGATTG      1140
CATTGAAACA AAGGAGGACA TTATGGCTAA AAAACTAATT TATGTGTGTT TAAGTGTTTG     1200
TTTAGTGTTG ACCTGGGCTT TTAATGTAAA AGGGCAATCT GCTCATGCTG ATGGGAACAC     1260
GACAACGATC ATTGTCCACT ATTTTTGCCC TGCTGGTGAT TATCAACCTT GGAGTCTATG     1320
GATGTGGCCA AAAGACGGAG GTGGGGCTGA ATACGATTTC AATCAACCGG CTGACTCTTT     1380
TGGAGCTGTT GCAAGTGCTG ATATTCCAGG AAACCCAAGT CAGGTAGGAA TTATCGTTCG     1440
CACTCAAGAT TGGACCAAAG ATGTGAGCGC TGACCGCTAC ATAGATTTAA GCAAAGGAAA     1500
TGAGGTGTGG CTTGTAGAAG GAAACAGCCA AATTTTTTAT AATGAAAAG ATGCTGAGGA      1560
TGCAGCTAAA CCCGCTGTAA GCAACGCTTA TTTAGATGCT TCAAACCAGG TGCTGGTTAA     1620
ACTTAGCCAG CCGTTAACTC TTGGGGAAGG NNNAAGCGGC TTTACGGTTC ATGACGACAC     1680
AGCAAATAAG GATATTCCAG TGACATCTGT GAAGGATGCA AGTCTTGGTC AAGATGTAAC     1740
CGCTGTTTTG GCAGGTACCT TCCAACATAT TTTTGGAGGT TCCGATTGGG CACCTGATAA     1800
TCACAGTACT TTATTAAAAA AGGTGACTAA CAATCTCTAT CAATTCTCAG GAGATCTTCC     1860
TGAAGGAAAC TACCAATATA AAGTGGCTTT AAATGATAGC TGGAATAATC CGAGTTACCC     1920
ATCTGACAAC ATTAATTTAA CAGTCCCTGC CGGCGGTGCA CACGTCACTT TTCGTATAT      1980
TCCGTCCACT CATGCAGTCT ATGACACAAT TAATAATCCT AATGCGGATT TACAAGTAGA     2040
AAGCGGGGTT AAAACGGATC TCGTGACGGT TACTCTAGGG GAAGATCCAG ATGTGAGCCA     2100
TACTCTGTCC ATTCAAACAG ATGGCTATCA GGCAAAGCAG GTGATACCTC GTAATGTGCT     2160
TAATTCATCA CAGTACTACT ATTCAGGAGA TGATCTTGGG AATACCTATA CACAGAAAGC     2220
AACAACCTTT AAAGTCTGGG CACCAACTTC TACTCAAGTA AATGTTCTTC TTTATGACAG     2280
TGCAACGGGT TCTGTAACAA AAATCGTACC TATGACGGCA TCGGCCATG GTGTGTGGGA      2340
AGCAACGGTT AATCAAAACC TTGAAAATTG GTATTACATG TATGAGGTAA CAGGCCAAGG     2400
CTCTACCCGA ACGGCTGTTG ATCCTTATGC AACTGCGATT GCACCAAATG GAACGAGAGG     2460
CATGATTGTG GACCTGGCTA AAACAGATCC TGCTGGCTGG AACAGTGATA ACATATTAC      2520
GCCAAAGAAT ATAGAAGATG AGGTCATCTA TGAAATGGAT GTCCGTGACT TTTCCATTGA     2580
CCCTAATTCG GGTATGAAAA ATAAAGGGAA GTATTTGGCT CTTACAGAAA AGGAACAAA      2640
GGGCCCTGAC AACGTAAAGA CGGGGATAGA TTCCTTAAAA CAACTTGGGA TTACTCATGT     2700
TCAGCTTATG CCTGTTTTCG CATCTAACAG TGTCGATGAA ACTGATCCAA CCCAAGATAA     2760
TTGGGGTTAT GACCCTCGCA ACTATGATGT TCCTGAAGGG CAGTATGCTA CAAATGCGAA     2820
TGGTAATGCT CGTATAAAAG AGTTTAAGGA AATGGTTCTT TCACTCCATC GTGAACACAT     2880
TGGGGTTAAC ATGGATGTTG TCTATAATCA TACCTTTGCC ACGCAAATCT CTGACTTCGA     2940
TAAAATTGTA CCAGAATATT ATTACCGTAC GATGATGCAG GTAATTATAC CAACGGATCA     3000
```

-continued

```
GGTACTGGAA ATGAAATTGC ANGCNGAAAG GCCAATGGTT CAAAAATTTA TTATTGATTC    3060
CCTTAAGTAT TGGGTCAATG AGTATCATAT TGACGGCTTC CGTTTTGACT TAATGGCGCT    3120
GCTTGGAAAA GACACGATGT CCAAAGCTGC CTCGGAGCTT CATGCTATTA ATCCAGGAAT    3180
TGCACTTTAC GGTGAGCCAT GGACGGGTGG AACCTCTGCA CTGCCAGATG ATCAGCTTCT    3240
GACAAAAGGA GCTCAAAAAG GCATGGGAGT AGCGGTGTTT AATGACAATT TACGAAACGC    3300
GTTGGACGGC AATGTCTTTG ATTCTTCCGC TCAAGGTTTT GCGACAGGTG CAACAGGCTT    3360
AACTGATGCA ATTAAGAATG GCGTTGAGGG GAGTATTAAT GACTTTACCT CTTCACCAGG    3420
TGAGACAATT AACTATGTCA CAAGTCATGA TAACTACACC CTTTGGGACA AAATAGCCCT    3480
AAGCAATCCT AATGATTCCG AAGCGGATCG GATTAAAATG GATGAACTCG CACAAGCAGT    3540
TGTTATGACC TCACAAGGCG TTCCATTCAT GCAAGGCGGG GAAGAAATGC TTCGTANAAA    3600
AGGCGGCAAC GACAATAGTT ATAATGCAGG CGATGCGGTC AATGAGTTTG ATTGGAGCAG    3660
GAAAGCTCAA TATCCAGATG TTTTCAACTA TTATAGCGGG CTAATCCACC TTCGTCTTGA    3720
TCACCCAGCC TTCCGCATGA CGACAGCTAA TGAAATCAAT AGCCACCTCC AATTCCTAAA    3780
TAGTCCAGAG AACACAGTGG CCTATGAATT AACTGATCAT GTTAATAAAG ACAAATGGGG    3840
AAATATCATT GTTGTTTATA ACCCAAATAA AACTGTAGCA ACCATCAATT GCCGAGCGG    3900
GAAATGGGCA ATCAATGCTA CGAGCGGTAA GGTAGGAGAA TCCACCCTTG GTCAAGCAGA    3960
GGGAAGTGTC CAAGTACCAG GTATATCTAT GATGATCCTT CATCAAGAGG TAAGCCCAGA    4020
CCACGGTAAA AAGTAATAGA AAAAGTAAA ATCCCTCAA GATGTTTGAG GGGGATTTAG     4080
TTACTTATTA TCCAATTAAT TTGCGGCTTC GGTGTTTTCA ATGGGCTCCG TATCCGTTCG    4140
GTTGTGTGAT CGGACAAATG GGAGTGAATA GGTCACAAGA GCAGCAGCCA TTTCAAGCAG    4200
ACCAGCGAAA GTAAACATTC GTTCTGGTGC AAATCGGGTC ATCAACCAAC CGGTAATTGC    4260
TTGGAAATA GGGATGGACC CTGACATCAC GATAATCATA ATACTAATAA CACGACCGAA    4320
TAACTTAGGT GGAATAAGCG TATGGTTAAC GCTTGGAGCA ATAATATTAA CCGCCGTTTC    4380
ATGAGCGCCA ACAAGCACTA GAAGGGCTAA AATAACCCAT AAGTTGTGTG TAAATCCTAT    4440
AAAAAATAAC ATAAGGCCCT GCAG                                           4464
```

( 2 ) INFORMATION FOR SEQ ID NO:9:

( i ) SEQUENCE CHARACTERISTICS:
        ( A ) LENGTH: 4464 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO:9:

```
GGATCCTGTT AGACTATTTG AGGAGTTTGC AACACTTGAT GTTTATCCA AAGGAAGGGC     60
CGGAGATCAT CGCTGGTCGA GGTGCTTTCG GTGAAGCATT TTCGCTATTT TGGGTATAAC    120
CGGGCGCATT ACGATCAATT GTTGAAGAG CATCTTGATT TACTTCAAAA GCTGAATGCT     180
TCGAAAAGAA TAACATGGAG CGGGCTTTAT CGAACACCTA TACATGATGC AGATATCGCA    240
CCCCGCCCTG TTCAGAAAAA CATTCCTTTG TGGGTTGGGG TGGTGGGAC NMNTGAAASC     300
NS Y KCK Y YGT GCRNVSNNNT ATGGTGCCGG CTTAGCATGG GTATTTGTC AGGCGATTGG  360
CTTCGGTTTA AGGCACTTTC GGACCTTTAT CGGCAGGCCG GCCAACAAGC ANGGTATTCA    420
CCGAACGATC TGAAAGTAGG AGTGACAGGG CATGCGTTTA TTGGAAAGAC GTCGCAGCAG    480
```

| | | | | | |
|---|---|---|---|---|---|
| GCACTCAATG | ACTATTACCC | CTATCACGCG | AATTATTGGC | TAACACTGAA | CCAACAATTA | 540 |
| GGGCAGCCGT | TACCCCAGCA | ATACGTGAGG | GAATTTAATT | TATTAGCCTC | CCCAGAGCAA | 600 |
| GCCTTATATG | TGGAAGCTC | TCAACAAGTG | GGCAGGNAAA | AATTTTGCGC | CAACATGAGG | 660 |
| NATTTGGTNA | TAAACGTTTT | ATCGCACAGA | TCGACATTGG | CGGAATGCCC | TTTAAAACAG | 720 |
| TGGCCAAGAA | TATTGAGCGG | TTAGGCCACT | GAGGTTGCAC | CTGTCGTACG | AAGAGCAACA | 780 |
| AGAGGGTAAT | GGTAATAATC | TATTTAACTG | TTATTAGAA | AACTTGGTAT | CTGTTTAATT | 840 |
| AAATAACAGG | AGCCTGGAAG | TGGGCCAAGG | CTCCTTTCTA | GGGAAACCTT | TTTCTATTTA | 900 |
| TATAGGCGTT | GTTGCCTAAG | GCTAAAGTAG | GATTTTATTA | AAAATATAGG | AATTGCTCTT | 960 |
| TTATTCGACA | CAATTATTCA | ATGGAATACG | ATAAATGGA | GAGTGTATGT | AAGCGTTATA | 1020 |
| TTTTATTGGG | GGGCTGATAG | AAGAAAAGGG | ATGCGACAGG | GTCTATTAGC | TAGTTTGGTA | 1080 |
| TTCGATTTCA | GATCAATGCA | ACGTACGAGT | TTTTATTGA | CTGCTTTGTG | CAAGCGATTG | 1140 |
| CATTGAAACA | AAGGAGGACA | TT ATG GCT AAA AAA CTA ATT TAT GTG TGT | | | | 1189 |

```
                              Met Ala Lys Lys Leu Ile Tyr Val Cys
                                                              -25

TTA AGT GTT TGT TTA GTG TTG ACC TGG GCT TTT AAT GTA AAA GGG CAA      1237
Leu Ser Val Cys Leu Val Leu Thr Trp Ala Phe Asn Val Lys Gly Gln
-20              -15                -10                        -5

TCT GCT CAT GCT GAT GGG AAC ACG ACA ACG ATC ATT GTC CAC TAT TTT      1285
Ser Ala His Ala Asp Gly Asn Thr Thr Thr Ile Ile Val His Tyr Phe
           -1 +1            5                     10

TGC CCT GCT GGT GAT TAT CAA CCT TGG AGT CTA TGG ATG TGG CCA AAA      1333
Cys Pro Ala Gly Asp Tyr Gln Pro Trp Ser Leu Trp Met Trp Pro Lys
         15                20                     25

GAC GGA GGT GGG GCT GAA TAC GAT TTC AAT CAA CCG GCT GAC TCT TTT      1381
Asp Gly Gly Gly Ala Glu Tyr Asp Phe Asn Gln Pro Ala Asp Ser Phe
     30                35                     40

GGA GCT GTT GCA AGT GCT GAT ATT CCA GGA AAC CCA AGT CAG GTA GGA      1429
Gly Ala Val Ala Ser Ala Asp Ile Pro Gly Asn Pro Ser Gln Val Gly
45               50                 55                        60

ATT ATC GTT CGC ACT CAA GAT TGG ACC AAA GAT GTG AGC GCT GAC CGC      1477
Ile Ile Val Arg Thr Gln Asp Trp Thr Lys Asp Val Ser Ala Asp Arg
             65                70                             75

TAC ATA GAT TTA AGC AAA GGA AAT GAG GTG TGG CTT GTA GAA GGA AAC      1525
Tyr Ile Asp Leu Ser Lys Gly Asn Glu Val Trp Leu Val Glu Gly Asn
         80                 85                         90

AGC CAA ATT TTT TAT AAT GAA AAA GAT GCT GAG GAT GCA GCT AAA CCC      1573
Ser Gln Ile Phe Tyr Asn Glu Lys Asp Ala Glu Asp Ala Ala Lys Pro
     95                100                    105

GCT GTA AGC AAC GCT TAT TTA GAT GCT TCA AAC CAG GTG CTG GTT AAA      1621
Ala Val Ser Asn Ala Tyr Leu Asp Ala Ser Asn Gln Val Leu Val Lys
110              115                120

CTT AGC CAG CCG TTA ACT CTT GGG GAA GGN NNA AGC GGC TTT ACG GTT      1669
Leu Ser Gln Pro Leu Thr Leu Gly Glu Gly Xaa Ser Gly Phe Thr Val
125              130                135                       140

CAT GAC GAC ACA GCA AAT AAG GAT ATT CCA GTG ACA TCT GTG AAG GAT      1717
His Asp Asp Thr Ala Asn Lys Asp Ile Pro Val Thr Ser Val Lys Asp
             145                150                       155

GCA AGT CTT GGT CAA GAT GTA ACC GCT GTT TTG GCA GGT ACC TTC CAA      1765
Ala Ser Leu Gly Gln Asp Val Thr Ala Val Leu Ala Gly Thr Phe Gln
         160                165                    170

CAT ATT TTT GGA GGT TCC GAT TGG GCA CCT GAT AAT CAC AGT ACT TTA      1813
His Ile Phe Gly Gly Ser Asp Trp Ala Pro Asp Asn His Ser Thr Leu
         175                180                    185

TTA AAA AAG GTG ACT AAC AAT CTC TAT CAA TTC TCA GGA GAT CTT CCT      1861
Leu Lys Lys Val Thr Asn Asn Leu Tyr Gln Phe Ser Gly Asp Leu Pro
     190                195                    200
```

```
GAA GGA AAC TAC CAA TAT AAA GTG GCT TTA AAT GAT AGC TGG AAT AAT    1909
Glu Gly Asn Tyr Gln Tyr Lys Val Ala Leu Asn Asp Ser Trp Asn Asn
205             210                 215                 220

CCG AGT TAC CCA TCT GAC AAC ATT AAT TTA ACA GTC CCT GCC GGC GGT    1957
Pro Ser Tyr Pro Ser Asp Asn Ile Asn Leu Thr Val Pro Ala Gly Gly
                225                 230                 235

GCA CAC GTC ACT TTT TCG TAT ATT CCG TCC ACT CAT GCA GTC TAT GAC    2005
Ala His Val Thr Phe Ser Tyr Ile Pro Ser Thr His Ala Val Tyr Asp
                240                 245                 250

ACA ATT AAT AAT CCT AAT GCG GAT TTA CAA GTA GAA AGC GGG GTT AAA    2053
Thr Ile Asn Asn Pro Asn Ala Asp Leu Gln Val Glu Ser Gly Val Lys
        255                 260                 265

ACG GAT CTC GTG ACG GTT ACT CTA GGG GAA GAT CCA GAT GTG AGC CAT    2101
Thr Asp Leu Val Thr Val Thr Leu Gly Glu Asp Pro Asp Val Ser His
        270                 275                 280

ACT CTG TCC ATT CAA ACA GAT GGC TAT CAG GCA AAG CAG GTG ATA CCT    2149
Thr Leu Ser Ile Gln Thr Asp Gly Tyr Gln Ala Lys Gln Val Ile Pro
285             290                 295                 300

CGT AAT GTG CTT AAT TCA TCA CAG TAC TAC TAT TCA GGA GAT GAT CTT    2197
Arg Asn Val Leu Asn Ser Ser Gln Tyr Tyr Tyr Ser Gly Asp Asp Leu
                305                 310                 315

GGG AAT ACC TAT ACA CAG AAA GCA ACA ACC TTT AAA GTC TGG GCA CCA    2245
Gly Asn Thr Tyr Thr Gln Lys Ala Thr Thr Phe Lys Val Trp Ala Pro
                320                 325                 330

ACT TCT ACT CAA GTA AAT GTT CTT CTT TAT GAC AGT GCA ACG GGT TCT    2293
Thr Ser Thr Gln Val Asn Val Leu Leu Tyr Asp Ser Ala Thr Gly Ser
        335                 340                 345

GTA ACA AAA ATC GTA CCT ATG ACG GCA TCG GGC CAT GGT GTG TGG GAA    2341
Val Thr Lys Ile Val Pro Met Thr Ala Ser Gly His Gly Val Trp Glu
350             355                 360

GCA ACG GTT AAT CAA AAC CTT GAA AAT TGG TAT TAC ATG TAT GAG GTA    2389
Ala Thr Val Asn Gln Asn Leu Glu Asn Trp Tyr Tyr Met Tyr Glu Val
365             370                 375                 380

ACA GGC CAA GGC TCT ACC CGA ACG GCT GTT GAT CCT TAT GCA ACT GCG    2437
Thr Gly Gln Gly Ser Thr Arg Thr Ala Val Asp Pro Tyr Ala Thr Ala
                385                 390                 395

ATT GCA CCA AAT GGA ACG AGA GGC ATG ATT GTG GAC CTG GCT AAA ACA    2485
Ile Ala Pro Asn Gly Thr Arg Gly Met Ile Val Asp Leu Ala Lys Thr
                400                 405                 410

GAT CCT GCT GGC TGG AAC AGT GAT AAA CAT ATT ACG CCA AAG AAT ATA    2533
Asp Pro Ala Gly Trp Asn Ser Asp Lys His Ile Thr Pro Lys Asn Ile
        415                 420                 425

GAA GAT GAG GTC ATC TAT GAA ATG GAT GTC CGT GAC TTT TCC ATT GAC    2581
Glu Asp Glu Val Ile Tyr Glu Met Asp Val Arg Asp Phe Ser Ile Asp
        430                 435                 440

CCT AAT TCG GGT ATG AAA AAT AAA GGG AAG TAT TTG GCT CTT ACA GAA    2629
Pro Asn Ser Gly Met Lys Asn Lys Gly Lys Tyr Leu Ala Leu Thr Glu
445             450                 455                 460

AAA GGA ACA AAG GGC CCT GAC AAC GTA AAG ACG GGG ATA GAT TCC TTA    2677
Lys Gly Thr Lys Gly Pro Asp Asn Val Lys Thr Gly Ile Asp Ser Leu
                465                 470                 475

AAA CAA CTT GGG ATT ACT CAT GTT CAG CTT ATG CCT GTT TTC GCA TCT    2725
Lys Gln Leu Gly Ile Thr His Val Gln Leu Met Pro Val Phe Ala Ser
                480                 485                 490

AAC AGT GTC GAT GAA ACT GAT CCA ACC CAA GAT AAT TGG GGT TAT GAC    2773
Asn Ser Val Asp Glu Thr Asp Pro Thr Gln Asp Asn Trp Gly Tyr Asp
            495                 500                 505

CCT CGC AAC TAT GAT GTT CCT GAA GGG CAG TAT GCT ACA AAT GCG AAT    2821
Pro Arg Asn Tyr Asp Val Pro Glu Gly Gln Tyr Ala Thr Asn Ala Asn
510                 515                 520
```

```
GGT AAT GCT CGT ATA AAA GAG TTT AAG GAA ATG GTT CTT TCA CTC CAT    2869
Gly Asn Ala Arg Ile Lys Glu Phe Lys Glu Met Val Leu Ser Leu His
525             530             535                 540

CGT GAA CAC ATT GGG GTT AAC ATG GAT GTT GTC TAT AAT CAT ACC TTT    2917
Arg Glu His Ile Gly Val Asn Met Asp Val Val Tyr Asn His Thr Phe
                545             550                 555

GCC ACG CAA ATC TCT GAC TTC GAT AAA ATT GTA CCA GAA TAT TAT TAC    2965
Ala Thr Gln Ile Ser Asp Phe Asp Lys Ile Val Pro Glu Tyr Tyr Tyr
            560             565                 570

CGT ACG ATG ATG CAG GTA ATT ATA CCA ACG GAT CAG GTA CTG GAA ATG    3013
Arg Thr Met Met Gln VaL Ile Ile Pro Thr Asp Gln Val Leu Glu Met
        575             580                 585

AAA TTG CAN GCN GAA AGG CCA ATG GTT CAA AAA TTT ATT ATT GAT TCC    3061
Lys Leu Xaa Ala Glu Arg Pro Met Val Gln Lys Phe Ile Ile Asp Ser
    590             595                 600

CTT AAG TAT TGG GTC AAT GAG TAT CAT ATT GAC GGC TTC CGT TTT GAC    3109
Leu Lys Tyr Trp Val Asn Glu Tyr His Ile Asp Gly Phe Arg Phe Asp
605             610             615                 620

TTA ATG GCG CTG CTT GGA AAA GAC ACG ATG TCC AAA GCT GCC TCG GAG    3157
Leu Met Ala Leu Leu Gly Lys Asp Thr Met Ser Lys Ala Ala Ser Glu
            625             630             635

CTT CAT GCT ATT AAT CCA GGA ATT GCA CTT TAC GGT GAG CCA TGG ACG    3205
Leu His Ala Ile Asn Pro Gly Ile Ala Leu Tyr Gly Glu Pro Trp Thr
        640             645                 650

GGT GGA ACC TCT GCA CTG CCA GAT GAT CAG CTT CTG ACA AAA GGA GCT    3253
Gly Gly Thr Ser Ala Leu Pro Asp Asp Gln Leu Leu Thr Lys Gly Ala
    655             660             665

CAA AAA GGC ATG GGA GTA GCG GTG TTT AAT GAC AAT TTA CGA AAC GCG    3301
Gln Lys Gly Met Gly Val Ala Val Phe Asn Asp Asn Leu Arg Asn Ala
670             675             680

TTG GAC GGC AAT GTC TTT GAT TCT TCC GCT CAA GGT TTT GCG ACA GGT    3349
Leu Asp Gly Asn Val Phe Asp Ser Ser Ala Gln Gly Phe Ala Thr Gly
685             690             695                 700

GCA ACA GGC TTA ACT GAT GCA ATT AAG AAT GGC GTT GAG GGG AGT ATT    3397
Ala Thr Gly Leu Thr Asp Ala Ile Lys Asn Gly Val Glu Gly Ser Ile
            705             710                 715

AAT GAC TTT ACC TCT TCA CCA GGT GAG ACA ATT AAC TAT GTC ACA AGT    3445
Asn Asp Phe Thr Ser Ser Pro Gly Glu Thr Ile Asn Tyr Val Thr Ser
        720             725                 730

CAT GAT AAC TAC ACC CTT TGG GAC AAA ATA GCC CTA AGC AAT CCT AAT    3493
His Asp Asn Tyr Thr Leu Trp Asp Lys Ile Ala Leu Ser Asn Pro Asn
    735             740                 745

GAT TCC GAA GCG GAT CGG ATT AAA ATG GAT GAA CTC GCA CAA GCA GTT    3541
Asp Ser Glu Ala Asp Arg Ile Lys Met Asp Glu Leu Ala Gln Ala Val
750             755                 760

GTT ATG ACC TCA CAA GGC GTT CCA TTC ATG CAA GGC GGG GAA GAA ATG    3589
Val Met Thr Ser Gln Gly Val Pro Phe Met Gln Gly Gly Glu Glu Met
765             770                 775                 780

CTT CGT ANA AAA GGC GGC AAC GAC AAT AGT TAT AAT GCA GGC GAT GCG    3637
Leu Arg Xaa Lys Gly Gly Asn Asp Asn Ser Tyr Asn Ala Gly Asp Ala
            785             790                 795

GTC AAT GAG TTT GAT TGG AGC AGG AAA GCT CAA TAT CCA GAT GTT TTC    3685
Val Asn Glu Phe Asp Trp Ser Arg Lys Ala Gln Tyr Pro Asp Val Phe
        800             805                 810

AAC TAT TAT AGC GGG CTA ATC CAC CTT CGT CTT GAT CAC CCA GCC TTC    3733
Asn Tyr Tyr Ser Gly Leu Ile His Leu Arg Leu Asp His Pro Ala Phe
    815             820                 825

CGC ATG ACG ACA GCT AAT GAA ATC AAT AGC CAC CTC CAA TTC CTA AAT    3781
Arg Met Thr Thr Ala Asn Glu Ile Asn Ser His Leu Gln Phe Leu Asn
830             835                 840
```

```
AGT CCA GAG AAC ACA GTG GCC TAT GAA TTA ACT GAT CAT GTT AAT AAA    3829
Ser Pro Glu Asn Thr Val Ala Tyr Glu Leu Thr Asp His Val Asn Lys
845                 850                 855                 860

GAC AAA TGG GGA AAT ATC ATT GTT GTT TAT AAC CCA AAT AAA ACT GTA    3877
Asp Lys Trp Gly Asn Ile Ile Val Val Tyr Asn Pro Asn Lys Thr Val
                865                 870                 875

GCA ACC ATC AAT TTG CCG AGC GGG AAA TGG GCA ATC AAT GCT ACG AGC    3925
Ala Thr Ile Asn Leu Pro Ser Gly Lys Trp Ala Ile Asn Ala Thr Ser
            880                 885                 890

GGT AAG GTA GGA GAA TCC ACC CTT GGT CAA GCA GAG GGA AGT GTC CAA    3973
Gly Lys Val Gly Glu Ser Thr Leu Gly Gln Ala Glu Gly Ser Val Gln
        895                 900                 905

GTA CCA GGT ATA TCT ATG ATG ATC CTT CAT CAA GAG GTA AGC CCA GAC    4021
Val Pro Gly Ile Ser Met Met Ile Leu His Gln Glu Val Ser Pro Asp
    910                 915                 920

CAC GGT AAA AAG TAATAGAAAA AAGTAAAATC CCCTCAAGAT GTTGAGGGG         4073
His Gly Lys Lys
925

GATTTAGTTA CTTATTATCC AATTAATTTG CGGCTTCGGT GTTTCAATG GCTCCGTAT    4133

CCGTTCGGTT GTGTGATCGG ACAAATGGGA GTGAATAGGT CACAAGAGCA GCAGCCATTT  4193

CAAGCAGACC AGCGAAAGTA AACATTCGTT CTGGTGCAAA TCGGGTCATC AACCAACCGG  4253

TAATTGCTTG GGAAATAGGG ATGGACCCTG ACATCACGAT AATCATAATA CTAATAACAC  4313

GACCGAATAA CTTAGGTGGA ATAAGCGTAT GGTTAACGCT TGGAGCAATA ATATTAACCG  4373

CCGTTTCATG AGCGCCAACA AGCACTAGAA GGGCTAAAAT AACCCATAAG TTGTGTGTAA  4433

ATCCTATAAA AAATAACATA AGGCCCTGCA G                                4464

( 2 ) INFORMATION FOR SEQ ID NO:10:

( i ) SEQUENCE CHARACTERISTICS:
        ( A ) LENGTH: 2784 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO:10:

GATGGGAACA CGACAACGAT CATTGTCCAC TATTTTTGCC CTGCTGGTGA TTATCAACCT   60

TGGAGTCTAT GGATGTGGCC AAAAGACGGA GGTGGGGCTG AATACGATTT CAATCAACCG   120

GCTGACTCTT TTGGAGCTGT TGCAAGTGCT GATATTCCAG GAAACCCAAG TCAGGTAGGA   180

ATTATCGTTC GCACTCAAGA TTGGACCAAA GATGTGAGCG CTGACCGCTA CATAGATTTA   240

AGCAAAGGAA ATGAGGTGTG GCTTGTAGAA GGAAACAGCC AAATTTTTTA TAATGAAAAA   300

GATGCTGAGG ATGCAGCTAA ACCCGCTGTA AGCAACGCTT ATTTAGATGC TTCAAACCAG   360

GTGCTGGTTA AACTTAGCCA GCCGTTAACT CTTGGGGAAG GNNAAGCGG CTTTACGGTT    420

CATGACGACA CAGCAAATAA GGATATTCCA GTGACATCTG TGAAGGATGC AAGTCTTGGT   480

CAAGATGTAA CCGCTGTTTT GGCAGGTACC TTCCAACATA TTTTTGGAGG TTCCGATTGG   540

GCACCTGATA ATCACAGTAC TTTATTAAAA AAGGTGACTA ACAATCTCTA TCAATTCTCA   600

GGAGATCTTC CTGAAGGAAA CTACCAATAT AAAGTGGCTT TAAATGATAG CTGGAATAAT   660

CCGAGTTACC CATCTGACAA CATTAATTTA ACAGTCCCTG CCGGCGGTGC ACACGTCACT   720

TTTTCGTATA TTCCGTCCAC TCATGCAGTC TATGACACAA TTAATAATCC TAATGCGGAT   780

TTACAAGTAG AAAGCGGGGT TAAAACGGAT CTCGTGACGG TTACTCTAGG GGAAGATCCA   840
```

```
GATGTGAGCC  ATACTCTGTC  CATTCAAACA  GATGGCTATC  AGGCAAAGCA  GGTGATACCT   900
CGTAATGTGC  TTAATTCATC  ACAGTACTAC  TATTCAGGAG  ATGATCTTGG  GAATACCTAT   960
ACACAGAAAG  CAACAACCTT  TAAAGTCTGG  GCACCAACTT  CTACTCAAGT  AAATGTTCTT  1020
CTTTATGACA  GTGCAACGGG  TTCTGTAACA  AAAATCGTAC  CTATGACGGC  ATCGGGCCAT  1080
GGTGTGTGGG  AAGCAACGGT  TAATCAAAAC  CTTGAAAATT  GGTATTACAT  GTATGAGGTA  1140
ACAGGCCAAG  GCTCTACCCG  AACGGCTGTT  GATCCTTATG  CAACTGCGAT  TGCACCAAAT  1200
GGAACGAGAG  GCATGATTGT  GGACCTGGCT  AAAACAGATC  CTGCTGGCTG  GAACAGTGAT  1260
AAACATATTA  CGCCAAAGAA  TATAGAAGAT  GAGGTCATCT  ATGAAATGGA  TGTCCGTGAC  1320
TTTTCCATTG  ACCCTAATTC  GGGTATGAAA  AATAAAGGGA  AGTATTTGGC  TCTTACAGAA  1380
AAAGGAACAA  AGGGCCCTGA  CAACGTAAAG  ACGGGGATAG  ATTCCTTAAA  ACAACTTGGG  1440
ATTACTCATG  TTCAGCTTAT  GCCTGTTTTC  GCATCTAACA  GTGTCGATGA  AACTGATCCA  1500
ACCCAAGATA  ATTGGGGTTA  TGACCCTCGC  AACTATGATG  TTCCTGAAGG  GCAGTATGCT  1560
ACAAATGCGA  ATGGTAATGC  TCGTATAAAA  GAGTTTAAGG  AAATGGTTCT  TTCACTCCAT  1620
CGTGAACACA  TTGGGGTTAA  CATGGATGTT  GTCTATAATC  ATACCTTTGC  CACGCAAATC  1680
TCTGACTTCG  ATAAAATTGT  ACCAGAATAT  TATTACCGTA  CGATGATGCA  GTAATTATA   1740
CCAACGGATC  AGGTACTGGA  AATGAAATTG  CANGCNGAAA  GGCCAATGGT  TCAAAAATTT  1800
ATTATTGATT  CCCTTAAGTA  TTGGGTCAAT  GAGTATCATA  TTGACGGCTT  CCGTTTTGAC  1860
TTAATGGCGC  TGCTTGGAAA  AGACACGATG  TCCAAAGCTG  CCTCGGAGCT  TCATGCTATT  1920
AATCCAGGAA  TTGCACTTTA  CGGTGAGCCA  TGGACGGGTG  GAACCTCTGC  ACTGCCAGAT  1980
GATCAGCTTC  TGACAAAAGG  AGCTCAAAAA  GGCATGGGAG  TAGCGGTGTT  TAATGACAAT  2040
TTACGAAACG  CGTTGGACGG  CAATGTCTTT  GATTCTTCCG  CTCAAGGTTT  TGCGACAGGT  2100
GCAACAGGCT  TAACTGATGC  AATTAAGAAT  GGCGTTGAGG  GGAGTATTAA  TGACTTTACC  2160
TCTTCACCAG  GTGAGACAAT  TAACTATGTC  ACAAGTCATG  ATAACTACAC  CCTTTGGGAC  2220
AAAATAGCCC  TAAGCAATCC  TAATGATTCC  GAAGCGGATC  GGATTAAAAT  GGATGAACTC  2280
GCACAAGCAG  TTGTTATGAC  CTCACAAGGC  GTTCCATTCA  TGCAAGGCGG  GGAAGAAATG  2340
CTTCGTANAA  AAGGCGGCAA  CGACAATAGT  TATAATGCAG  GCGATGCGGT  CAATGAGTTT  2400
GATTGGAGCA  GGAAAGCTCA  ATATCCAGAT  GTTTCAACT   ATTATAGCGG  CTAATCCAC   2460
CTTCGTCTTG  ATCACCCAGC  CTTCCGCATG  ACGACAGCTA  ATGAAATCAA  TAGCCACCTC  2520
CAATTCCTAA  ATAGTCCAGA  GAACACAGTG  GCCTATGAAT  TAACTGATCA  TGTTAATAAA  2580
GACAAATGGG  GAAATATCAT  TGTTGTTTAT  AACCCAAATA  AAACTGTAGC  AACCATCAAT  2640
TTGCCGAGCG  GGAAATGGGC  AATCAATGCT  ACGAGCGGTA  AGGTAGGAGA  ATCCACCCTT  2700
GGTCAAGCAG  AGGGAAGTGT  CCAAGTACCA  GGTATATCTA  TGATGATCCT  TCATCAAGAG  2760
GTAAGCCCAG  ACCACGGTAA  AAAG                                            2784
```

( 2 ) INFORMATION FOR SEQ ID NO:11:

( i ) SEQUENCE CHARACTERISTICS:
        ( A ) LENGTH: 928 amino acids
        ( B ) TYPE: amino acids
        ( D ) TOPOLOGY: linear ( i i ) MOLECULE TYPE: protein ( x i ) SEQUENCE DESCRIPTION: SEQ ID NO:11:

```
Asp  Gly  Asn  Thr  Thr  Thr  Ile  Ile  Val  His  Tyr  Phe  Cys  Pro  Ala  Gly
 1              5                        10                       15
```

| | | | | | | | | | | | | | | |
|---|---|---|---|---|---|---|---|---|---|---|---|---|---|---|
| Asp | Tyr | Gln | Pro<br>20 | Trp | Ser | Leu | Trp | Met<br>25 | Trp | Pro | Lys | Asp<br>30 | Gly | Gly |
| Ala | Glu | Tyr<br>35 | Asp | Phe | Asn | Gln | Pro<br>40 | Ala | Asp | Ser | Phe | Gly<br>45 | Ala | Val | Ala |
| Ser | Ala<br>50 | Asp | Ile | Pro | Gly | Asn<br>55 | Pro | Ser | Gln | Val | Gly<br>60 | Ile | Ile | Val | Arg |
| Thr<br>65 | Gln | Asp | Trp | Thr | Lys<br>70 | Asp | Val | Ser | Ala | Asp<br>75 | Arg | Tyr | Ile | Asp | Leu<br>80 |
| Ser | Lys | Gly | Asn | Glu<br>85 | Val | Trp | Leu | Val | Gly<br>90 | Asn | Ser | Gln | Ile<br>95 | Phe |
| Tyr | Asn | Glu | Lys<br>100 | Asp | Ala | Glu | Asp | Ala<br>105 | Lys | Pro | Ala | Val<br>110 | Ser | Asn |
| Ala | Tyr | Leu<br>115 | Asp | Ala | Ser | Asn | Gln<br>120 | Val | Leu | Val | Lys | Leu<br>125 | Ser | Gln | Pro |
| Leu | Thr<br>130 | Leu | Gly | Glu | Gly | Xaa<br>135 | Ser | Gly | Phe | Thr | Val<br>140 | His | Asp | Asp | Thr |
| Ala<br>145 | Asn | Lys | Asp | Ile | Pro<br>150 | Val | Thr | Ser | Val | Lys<br>155 | Asp | Ala | Ser | Leu | Gly<br>160 |
| Gln | Asp | Val | Thr | Ala<br>165 | Val | Leu | Ala | Gly | Thr<br>170 | Phe | Gln | His | Ile | Phe<br>175 | Gly |
| Gly | Ser | Asp | Trp<br>180 | Ala | Pro | Asp | Asn | His<br>185 | Ser | Thr | Leu | Leu | Lys<br>190 | Lys | Val |
| Thr | Asn | Asn<br>195 | Leu | Tyr | Gln | Phe | Ser<br>200 | Gly | Asp | Leu | Pro | Glu<br>205 | Gly | Asn | Tyr |
| Gln | Tyr<br>210 | Lys | Val | Ala | Leu | Asn<br>215 | Asp | Ser | Trp | Asn | Asn<br>220 | Pro | Ser | Tyr | Pro |
| Ser<br>225 | Asp | Asn | Ile | Asn | Leu<br>230 | Thr | Val | Pro | Ala | Gly<br>235 | Gly | Ala | His | Val | Thr<br>240 |
| Phe | Ser | Tyr | Ile | Pro<br>245 | Ser | Thr | His | Ala | Val<br>250 | Tyr | Asp | Thr | Ile | Asn<br>255 | Asn |
| Pro | Asn | Ala | Asp<br>260 | Leu | Gln | Val | Glu | Ser<br>265 | Gly | Val | Lys | Thr<br>270 | Asp | Leu | Val |
| Thr | Val | Thr<br>275 | Leu | Gly | Glu | Asp | Pro<br>280 | Asp | Val | Ser | His | Thr<br>285 | Leu | Ser | Ile |
| Gln | Thr<br>290 | Asp | Gly | Tyr | Gln | Ala<br>295 | Lys | Gln | Val | Ile | Pro<br>300 | Arg | Asn | Val | Leu |
| Asn<br>305 | Ser | Ser | Gln | Tyr | Tyr<br>310 | Tyr | Ser | Gly | Asp | Asp<br>315 | Leu | Gly | Asn | Thr | Tyr<br>320 |
| Thr | Gln | Lys | Ala | Thr<br>325 | Thr | Phe | Lys | Val | Trp<br>330 | Ala | Pro | Thr | Ser | Thr<br>335 | Gln |
| Val | Asn | Val | Leu<br>340 | Leu | Tyr | Asp | Ser | Ala<br>345 | Thr | Gly | Ser | Val<br>350 | Thr | Lys | Ile |
| Val | Pro | Met<br>355 | Thr | Ala | Ser | Gly | His<br>360 | Gly | Val | Trp | Glu | Ala<br>365 | Thr | Val | Asn |
| Gln | Asn<br>370 | Leu | Glu | Asn | Trp | Tyr<br>375 | Tyr | Met | Tyr | Glu | Val<br>380 | Thr | Gly | Gln | Gly |
| Ser<br>385 | Thr | Arg | Thr | Ala | Val<br>390 | Asp | Pro | Tyr | Ala | Thr<br>395 | Ala | Ile | Ala | Pro | Asn<br>400 |
| Gly | Thr | Arg | Gly | Met<br>405 | Ile | Val | Asp | Leu | Ala<br>410 | Lys | Thr | Asp | Pro | Ala<br>415 | Gly |
| Trp | Asn | Ser | Asp<br>420 | Lys | His | Ile | Thr | Pro<br>425 | Lys | Asn | Ile | Glu<br>430 | Asp | Glu | Val |
| Ile | Tyr | Glu | Met | Asp | Val | Arg | Asp | Phe | Ser | Ile | Asp | Pro | Asn | Ser | Gly |

```
                    435                    440                    445
Met Lys Asn Lys Gly Lys Tyr Leu Ala Leu Thr Glu Lys Gly Thr Lys
    450                 455                 460
Gly Pro Asp Asn Val Lys Thr Gly Ile Asp Ser Leu Lys Gln Leu Gly
465                 470                 475                     480
Ile Thr His Val Gln Leu Met Pro Val Phe Ala Ser Asn Ser Val Asp
                    485                 490                 495
Glu Thr Asp Pro Thr Gln Asp Asn Trp Gly Tyr Asp Pro Arg Asn Tyr
            500                 505                 510
Asp Val Pro Glu Gly Gln Tyr Ala Thr Asn Ala Asn Gly Asn Ala Arg
            515                 520                 525
Ile Lys Glu Phe Lys Glu Met Val Leu Ser Leu His Arg Glu His Ile
    530                 535                 540
Gly Val Asn Met Asp Val Val Tyr Asn His Thr Phe Ala Thr Gln Ile
545                 550                 555                     560
Ser Asp Phe Asp Lys Ile Val Pro Glu Tyr Tyr Tyr Arg Thr Met Met
                565                 570                 575
Gln Val Ile Ile Pro Thr Asp Gln Val Leu Glu Met Lys Leu Xaa Ala
            580                 585                 590
Glu Arg Pro Met Val Gln Lys Phe Ile Ile Asp Ser Leu Lys Tyr Trp
        595                 600                 605
Val Asn Glu Tyr His Ile Asp Gly Phe Arg Phe Asp Leu Met Ala Leu
610                 615                 620
Leu Gly Lys Asp Thr Met Ser Lys Ala Ala Ser Glu Leu His Ala Ile
625                 630                 635                     640
Asn Pro Gly Ile Ala Leu Tyr Gly Glu Pro Trp Thr Gly Gly Thr Ser
                    645                 650                 655
Ala Leu Pro Asp Asp Gln Leu Leu Thr Lys Gly Ala Gln Lys Gly Met
            660                 665                 670
Gly Val Ala Val Phe Asn Asp Asn Leu Arg Asn Ala Leu Asp Gly Asn
        675                 680                 685
Val Phe Asp Ser Ser Ala Gln Gly Phe Ala Thr Gly Ala Thr Gly Leu
    690                 695                 700
Thr Asp Ala Ile Lys Asn Gly Val Glu Gly Ser Ile Asn Asp Phe Thr
705                 710                 715                     720
Ser Ser Pro Gly Glu Thr Ile Asn Tyr Val Thr Ser His Asp Asn Tyr
            725                 730                 735
Thr Leu Trp Asp Lys Ile Ala Leu Ser Asn Pro Asn Asp Ser Glu Ala
            740                 745                 750
Asp Arg Ile Lys Met Asp Glu Leu Ala Gln Ala Val Val Met Thr Ser
        755                 760                 765
Gln Gly Val Pro Phe Met Gln Gly Gly Glu Glu Met Leu Arg Xaa Lys
    770                 775                 780
Gly Gly Asn Asp Asn Ser Tyr Asn Ala Gly Asp Ala Val Asn Glu Phe
785                 790                 795                     800
Asp Trp Ser Arg Lys Ala Gln Tyr Pro Asp Val Phe Asn Tyr Tyr Ser
                805                 810                 815
Gly Leu Ile His Leu Arg Leu Asp His Pro Ala Phe Arg Met Thr Thr
            820                 825                 830
Ala Asn Glu Ile Asn Ser His Leu Gln Phe Leu Asn Ser Pro Glu Asn
            835                 840                 845
Thr Val Ala Tyr Glu Leu Thr Asp His Val Asn Lys Asp Lys Trp Gly
    850                 855                 860
```

| | | | | | | | | | | | | | | |
|---|---|---|---|---|---|---|---|---|---|---|---|---|---|---|
| Asn | Ile | Ile | Val | Val | Tyr | Asn | Pro | Asn | Lys | Thr | Val | Ala | Thr | Ile | Asn |
| 865 | | | | | 870 | | | | | 875 | | | | | 880 |

| Leu | Pro | Ser | Gly | Lys | Trp | Ala | Ile | Asn | Ala | Thr | Ser | Gly | Lys | Val | Gly |
|---|---|---|---|---|---|---|---|---|---|---|---|---|---|---|---|
| | | | | 885 | | | | | 890 | | | | | 895 | |

| Glu | Ser | Thr | Leu | Gly | Gln | Ala | Glu | Gly | Ser | Val | Gln | Val | Pro | Gly | Ile |
|---|---|---|---|---|---|---|---|---|---|---|---|---|---|---|---|
| | | | 900 | | | | 905 | | | | | 910 | | | |

| Ser | Met | Met | Ile | Leu | His | Gln | Glu | Val | Ser | Pro | Asp | His | Gly | Lys | Lys |
|---|---|---|---|---|---|---|---|---|---|---|---|---|---|---|---|
| | | 915 | | | | 920 | | | | | 925 | | | | |

( 2 ) INFORMATION FOR SEQ ID NO:12:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:12:

| Met | Ala | Lys | Lys | Leu | Ile | Tyr | Val | Cys | Leu | Ser | Val | Cys | Leu | Val | Leu |
|---|---|---|---|---|---|---|---|---|---|---|---|---|---|---|---|
| | | | | -25 | | | | -20 | | | | | -15 | | |

| Thr | Trp | Ala | Phe | Asn | Val | Lys | Gly | Gln | Ser | Ala | His | Ala |
|---|---|---|---|---|---|---|---|---|---|---|---|---|
| | | | -10 | | | | | -5 | | | | -1 |

( 2 ) INFORMATION FOR SEQ ID NO:13:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i i ) MOLECULE TYPE: nucleic acid ( x i ) SEQUENCE DESCRIPTION: SEQ ID NO:13:

```
ATG GCT AAA AAA CTA ATT TAT GTG TGT TTA AGT GTT TGT TTA GTG TTG      48
Met Ala Lys Lys Leu Ile Tyr Val Cys Leu Ser Val Cys Leu Val Leu
                -25              -20                  -15

ACC TGG GCT TTT AAT GTA AAA GGG CAA TCT GCT CAT GCT                  87
Thr Trp Ala Phe Asn Val Lys Gly Gln Ser Ala His Ala
            -10              -5              -1
```

( 2 ) INFORMATION FOR SEQ ID NO:14:

( i ) SEQUENCE CHARACTERISTICS:
        ( A ) LENGTH: 1162 base pairs
        ( B ) TYPE: nucleic acid
        ( C ) STRANDEDNESS: single
        ( D ) TOPOLOGY: linear ( i i ) MOLECULE TYPE: nucleic acid ( x i ) SEQUENCE DESCRIPTION: SEQ ID NO:14:

```
GGATCCTGTT AGACTATTTG AGGAGTTTGC AACACTTGAT GTTTATCCA  AAGGAAGGGC      60
CGGAGATCAT CGCTGGTCGA GGTGCTTTCG GTGAAGCATT TTCGCTATTT TGGGTATAAC    120
CGGGCGCATT ACGATCAATT GTTGAAGAG  CATCTTGATT TACTTCAAAA GCTGAATGCT    180
TCGAAAAGAA TAACATGGAG CGGGCTTTAT CGAACACCTA TACATGATGC AGATATCGCA    240
CCCCGCCCTG TTCAGAAAAA CATTCCTTTG TGGGTTGGGG TGGGTGGGAC NMNTGAAASC    300
NS Y KCK Y YGT GCRNVSNNNT ATGGTGCCGG CTTAGCATGG GTATTTGTC AGGCGATTGG  360
CTTCGGTTTA AGGCACTTTC GGACCTTTAT CGGCAGGCCG GCCAACAAGC ANGGTATTCA    420
CCGAACGATC TGAAAGTAGG AGTGACAGGG CATGCGTTTA TTGGAAAGAC GTCGCAGCAG    480
```

```
GCACTCAATG ACTATTACCC CTATCACGCG AATTATTGGC TAACACTGAA CCAACAATTA    540

GGGCAGCCGT TACCCCAGCA ATACGTGAGG GAATTTAATT TATTAGCCTC CCCAGAGCAA    600

GCCTTATATG TGGGAAGCTC TCAACAAGTG GGCAGGNAAA AATTTTGCGC CAACATGAGG    660

NATTTGGTNA TAAACGTTTT ATCGCACAGA TCGACATTGG CGGAATGCCC TTTAAAACAG    720

TGGCCAAGAA TATTGAGCGG TTAGGCCACT GAGGTTGCAC CTGTCGTACG AAGAGCAACA    780

AGAGGGTAAT GGTAATAATC TATTTAACTG TTTATTAGAA AACTTGGTAT CTGTTTAATT    840

AAATAACAGG AGCCTGGAAG TGGGCCAAGG CTCCTTTCTA GGGAAACCTT TTTCTATTTA    900

TATAGGCGTT GTTGCCTAAG GCTAAAGTAG GATTTTATTA AAAATATAGG AATTGCTCTT    960

TTATTCGACA CAATTATTCA ATGGAATACG ATAAAATGGA GAGTGTATGT AAGCGTTATA    1020

TTTTATTGGG GGGCTGATAG AAGAAAAGGG ATGCGACAGG GTCTATTAGC TAGTTTGGTA    1080

TTCGATTTCA GATCAATGCA ACGTACGAGT TTTTTATTGA CTGCTTTGTG CAAGCGATTG    1140

CATTGAAACA AAGGAGGACA TT                                             1162
```

( 2 ) INFORMATION FOR SEQ ID NO:15:

( i ) SEQUENCE CHARACTERISTICS:
        ( A ) LENGTH: 431 base pairs
        ( B ) TYPE: nucleic acid
        ( C ) STRANDEDNESS: single
        ( D ) TOPOLOGY: linear ( i i ) MOLECULE TYPE: nucleic acid ( x i ) SEQUENCE DESCRIPTION: SEQ ID NO:15:

```
TAATAGAAAA AAGTAAAATC CCCTCAAGAT GTTTGAGGGG GATTTAGTTA CTTATTATCC    60

AATTAATTTG CGGCTTCGGT GTTTTCAATG GGCTCCGTAT CCGTTCGGTT GTGTGATCGG    120

ACAAATGGGA GTGAATAGGT CACAAGAGCA GCAGCCATTT CAAGCAGACC AGCGAAAGTA    180

AACATTCGTT CTGGTGCAAA TCGGGTCATC AACCAACCGG TAATTGCTTG GGAAATAGGG    240

ATGGACCCTG ACATCACGAT AATCATAATA CTAATAACAC GACCGAATAA CTTAGGTGGA    300

ATAAGCGTAT GGTTAACGCT TGGAGCAATA ATATTAACCG CCGTTTCATG AGCGCCAACA    360

AGCACTAGAA GGGCTAAAAT AACCCATAAG TTGTGTGTAA ATCCTATAAA AAATAACATA    420

AGGCCCTGCA G                                                         431
```